US012573475B2

(12) United States Patent
Anand et al.

(10) Patent No.: US 12,573,475 B2
(45) Date of Patent: Mar. 10, 2026

(54) PROTEIN SEQUENCE AND STRUCTURE GENERATION WITH DENOISING DIFFUSION PROBABILISTIC MODELS

(71) Applicant: Diffuse Bio, Inc., San Carlos, CA (US)

(72) Inventors: Namrata Anand, Menlo Park, CA (US); Tudor Achim, Menlo Park, CA (US)

(73) Assignee: Diffuse Bio, Inc., San Carlos, CA (US)

( * ) Notice: Subject to any disclaimer, the term of this patent is extended or adjusted under 35 U.S.C. 154(b) by 0 days.

(21) Appl. No.: 18/199,144

(22) Filed: May 18, 2023

(65) Prior Publication Data

US 2023/0377690 A1     Nov. 23, 2023

Related U.S. Application Data

(60) Provisional application No. 63/343,789, filed on May 19, 2022.

(51) Int. Cl.
G16B 40/00          (2019.01)
G16B 15/00          (2019.01)

(52) U.S. Cl.
CPC ............. G16B 40/00 (2019.02); G16B 15/00 (2019.02)

(58) Field of Classification Search
CPC ................................. G16B 40/00; G16B 15/00
See application file for complete search history.

(56) References Cited

PUBLICATIONS

Torrisi et al. "Deep Learning Methods in Protein Structure Prediction" Computational and Structural Biotechnology Journal (2020) vol. 18, pp. 1301-1310 (Year: 2020).*
Akpinaroglu et al., Improved antibody structure prediction by deep learning of side chain conformations, BioRxiv, Sep. 17, 2021, pp. 1-16, https://doi.org/10.1101/2021.09.22.461349.
Alford et al., The Rosetta all-atom energy function for macromolecular modeling and design, Journal of Chemical Theory and Computation, 13(6), Feb. 7, 2017, pp. 1-35, https://doi.org/10.1101/106054.
Anand et al., Generative Modeling for Protein Structures, Advances in Neural Information Processing Systems, 31, 2018, pp. 1-12.
Anand et al., Protein sequence design with a learned potential, Nature Communications, 13(1):746, Feb. 8, 2022, pp. 1-11, https://doi.org/10.1038/s41467-022-28313-9.
Austin et al., Structured Denoising Diffusion Models in Discrete State-Spaces, Advances in Neural Information Processing Systems, 34, Dec. 6, 2021, pp. 1-33, arXiv:2017.03006v3 [cs.LG].
Berman et al., The Protein Data Bank, Nucleic Acids Research, vol. 28, Issue 1, Jan. 1, 2000, pp. 235-242, https://doi.org/10.1093/nar/28.1.235.
Brown et al., Language Models are Few-Shot Learners, Advances in Neural Information Processing Systems, vol. 33, Jul. 22, 2020, pp. 1877-1901, arXiv:2005.14165v4 [cs.CL].
Castro et al., ReLSO: A Transformer-based Model for Latent Space Optimization and Generation of Proteins, arXiv preprint, Jan. 24, 2022, pp. 1-25, arXiv:2201.09948v2 [cs.LG].
Dawson et al., CATH: an expanded resource to predict protein function through structure and sequence, Nucleic Acids Research, vol. 45, Issue D1, Jan. 2017, pp. D289-D295, https://doi.org/10.1093/nar/gkw1098.
De Bortoli et al., Riemannian Score-Based Generative Modeling, Advances in Neural Information Processing Systems, Nov. 22, 2022, 50 pages, arXiv:2202.02763 [cs.LG].
Devlin et al., BERT: Pre-training of Deep Bidirectional Transformers for Language Understanding, Proceedings of NAACL-HLT 2019, May 24, 2019, pp. 4171-4186.
Dhariwal et al., Diffusion Models Beat GANS on Image Synthesis, Advances in Neural Information Processing Systems, 34, Dec. 6, 2021, pp. 1-15.
Du et al., Energy-Based Models for Atomic-Resolution Protein Conformations, ICLR 2020 Conference Paper, Apr. 27, 2020, pp. 1-16, arXiv:2004.13167v1 [cs.LG].
Eguchi et al., IG-VAE: Generative Modeling of Immunoglobulin Proteins by Direct 3D Coordinate Generation, bioRxiv, Jan. 1, 2020, pp. 1-13, https://doi.org/10.1101/2020.08.07.242347.
Ferruz et al., A deep unsupervised language model for protein design, bioRxiv, Mar. 12, 2022, pp. 1-14, https://doi.org/10.1101/2022.03.09.483666.
Ferruz et al., Towards Controllable Protein Design with Conditional Transformers, arXiv preprint, 2022, pp. 1-17, arXiv:2201.07338.
Gao et al., AlphaDesign: A graph protein design method and benchmark on AlphaFoldDB, arXiv preprint, Feb. 12, 2022, 11 pages, arXiv:2202.01079v2 [q-bio.QM].
Ho et al., Denoising Diffusion Probabilistic Models, 34th Conference on Neural Information Processing Systems (NeurIPS 2020), Dec. 16, 2020, pp. 1-25, arXiv:2006.11239v2 [cs.LG].
Hsu et al., Learning inverse folding from millions of predicted structures, vioRxiv preprint, Systems Biology, Apr. 10, 2022, pp. 1-22, https://doi.org/10.1101/2022.04.10.487779.
Ingraham et al., Generative models for graph-based protein design, Advances in Neural Information Processing Systems, vol. 32, 2019, pp. 1-12.
Jing et al., Torsional Diffusion for Molecular Conformer Generation, ICLR2022 Machine Learning for Drug Discovery, Dec. 6, 2022, pp. 1-28, arXiv:2206.01729v2 [physics.chem-ph].
(Continued)

*Primary Examiner* — Jerry Lin
(74) *Attorney, Agent, or Firm* — Van Pelt, Yi & James LLP

(57)          ABSTRACT

Training a protein diffusion model includes receiving a representation of a protein as training data, the representation comprising at least three dimensions. It further includes training a protein diffusion model at least in part by performing rotational diffusion based at least in part on the representation of the protein.

Generating proteins includes receiving protein conditioning information. It further includes, based at least in part on the protein conditioning information, performing conditional sampling of a protein diffusion model. The protein diffusion model is trained at least in part by performing rotational diffusion. Based at least in part on the conditional sampling of the protein diffusion model, the protein diffusion model generates one or more of a protein structure or a protein sequence.

14 Claims, 20 Drawing Sheets

(56) References Cited

PUBLICATIONS

Jumper et al., Highly accurate protein structure prediction with AlphaFold, Nature, vol. 596, Aug. 26, 2021, pp. 583-589.

Kingma et al., "Adam: A Method for Stochastic Optimization", arXiv preprint, Dec. 22, 2014, pp. 1-15, arXiv:1412.6980v9 [cs. LG].

Kuhlman et al., Native protein sequences are close to optimal for their structures, Proceedings of the National Academy of Sciences, vol. 97, No. 19, Sep. 12, 2000, pp. 10383-10388.

Leaver-Fay et al., Scientific Benchmarks for Guiding Macromolecular Energy Function Improvement, Methods in Enzymology, vol. 523, Jan. 1, 2013, pp. 109-143.

Lewis et al., Gene3D: Extensive prediction of globular domains in proteins, Nucleic Acids Research, vol. 46, Database Issue, Nov. 3, 2017, pp. D435-D439.

Liu et al., Prediction of amino acid side chain conformation using a deep neural network, arXiv preprint, Jul. 26, 2017, 39 pages, arXiv:1707.08381.

Loshchilov et al., SGDR: Stochastic Gradient Descent with Warm Restarts, arXiv preprint, Aug. 13, 2016, pp. 1-16, arXiv:1608. 03983v5 [CS.LG].

Madani et al., ProGen: Language Modeling for Protein Generation, arXiv preprint, Mar. 8, 2020, 17 pages, arXiv:2004.03497v1 [q-bio. BM].

Mcpartlon et al., An end-to-end deep learning method for rotamer-free protein side-chain packing, bioRxiv preprint, Mar. 14, 2022, pp. 1-29, https://doi.org/10.1101/2022.03.11.483812.

Rohl et al., Protein Structure Prediction Using Rosetta, Methods in Enzymology, vol. 383, Jan. 1, 2004, pp. 66-93.

Shoemake, Animating Rotation with Quaternion Curves, Proceedings of the 12th Annual Conference on Computer Graphics and Interactive Techniques, vol. 19, No. 3, Jul. 1, 1985, pp. 245-254.

Sohl-Dickstein et al., Deep Unsupervised Learning using Nonequilibrium Thermodynamics, International Conference on Machine Learning, Jun. 1, 2015, pp. 2256-2265, arXiv:1503.03585v8 [cs. LG].

Strokach et al., Deep generative modeling for protein design, ScienceDirect, Current Opinion in Structural Biology, 72, Feb. 1, 2022, pp. 226-236.

Strokach et al., Fast and Flexible Protein Design Using Deep Graph Neural Networks, Cell Systems, 11, Oct. 21, 2020, pp. 402-411; https://doi.org/10.1016/j.cels.2020.08.016.

Xu et al., GeoDiff: A Geometric Diffusion Model for Molecular Conformation Generation, International Conference on Learning Representations, Mar. 6, 2022, pp. 1-19, arXiv:2023.02923v1 [cs. LG].

* cited by examiner

1602

1604

PROTEIN SEQUENCE AND STRUCTURE GENERATION WITH DENOISING DIFFUSION PROBABILISTIC MODELS

CROSS REFERENCE TO OTHER APPLICATIONS

This application claims priority to U.S. Provisional Patent Application No. 63/343,789 entitled PROTEIN SEQUENCE AND STRUCTURE GENERATION WITH DENOISING DIFFUSION PROBABILISTIC MODELS filed May 19, 2022 which is incorporated herein by reference for all purposes.

BACKGROUND OF THE INVENTION

Proteins are macromolecules that mediate a significant fraction of the cellular processes that underlie life. One critical task in bio-engineering and medicine is designing proteins with specific 3D (three-dimensional) structures and chemical properties which target downstream functions. Existing techniques for designing proteins are inefficient and burdensome.

BRIEF DESCRIPTION OF THE DRAWINGS

Various embodiments of the invention are disclosed in the following detailed description and the accompanying drawings.

DETAILED DESCRIPTION

Figure 1:
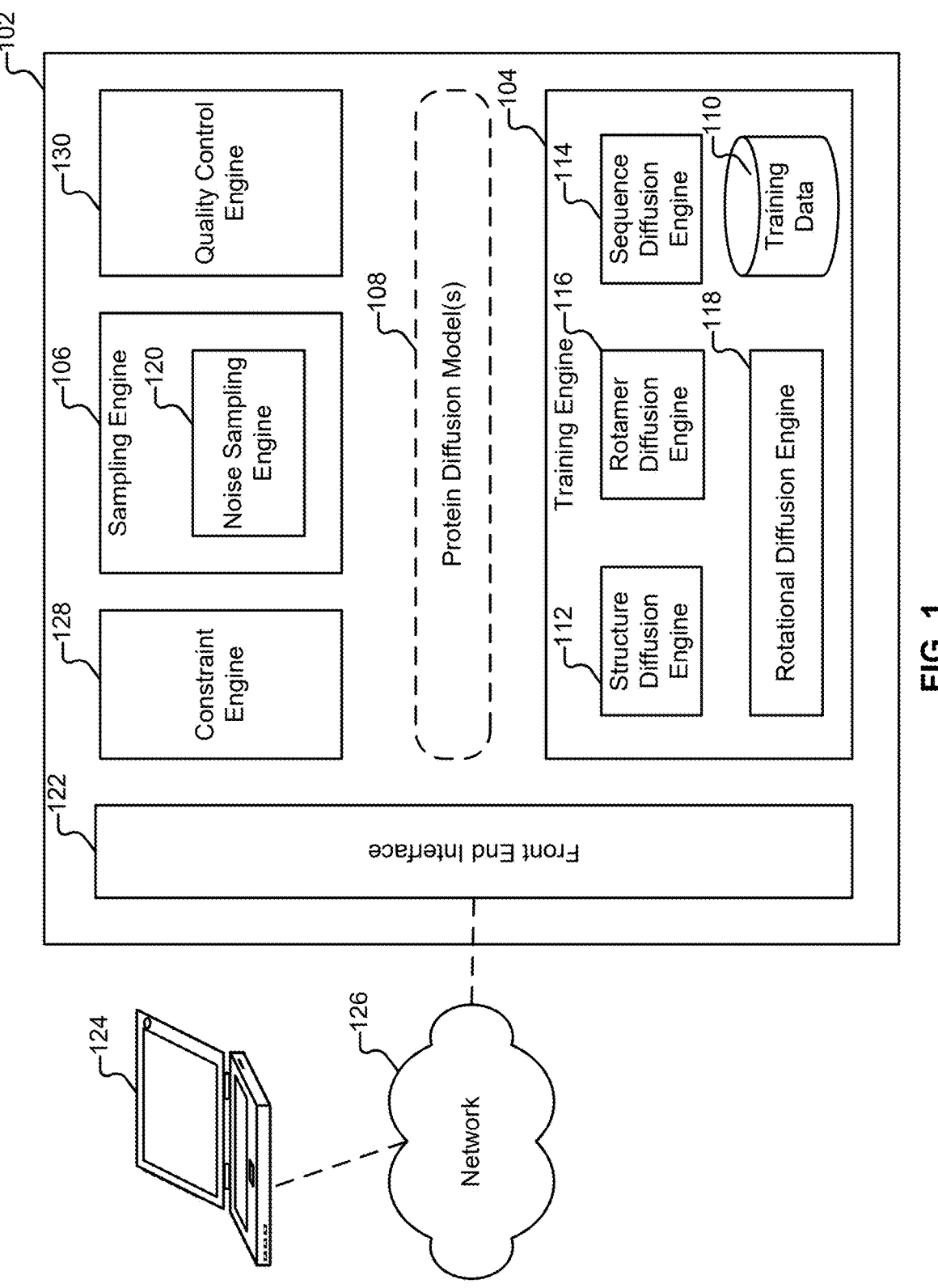
FIG. 1 illustrates an embodiment of a system for predicting protein structure and sequence.

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Described herein are embodiments of a generative model of both protein structure and sequence. In various embodiments, the model can be learned entirely from data and conditions on a compact specification of protein topology.

Proteins are large macromolecules that play fundamental roles in nearly all cellular processes. There are two key scientific challenges related to these molecules in the context of bio-engineering: characterizing the set of all naturally-occurring proteins based on sequences cheaply collected at scale, and designing new proteins whose structure and sequence achieve functional goals specified by the researcher. Recently, AlphaFold2, a purely data-driven machine learning approach, has become the state of the art for the forward problem of structure prediction. Similarly, machine learning approaches have come to perform well for the sequence generation inverse problem. However, for the task of de-novo structure generation, stochastic search algorithms based on handcrafted energy functions and heuristic sampling approaches are still in wide use.

Data-driven generative modeling approaches have not yet seen as much success in the protein modeling setting as they have in the image generation setting because of some key differences between the two. First, unlike images, proteins do not have a natural representation on a discretized grid that is amenable to straightforward applications of existing generative models. Interpreting the pairwise distance matrix of a protein as an image to be modeled with existing models has seen limited success because random errors in the predictions lead to nontrivial errors when optimization routines are used to recover the final structures. Second, unlike images, proteins have no natural canonical orientation frame. Ground-truth protein structures are typically obtained from X-ray crystallography or Cryogenic electron microscopy, which are unbiased with respect to the dominant orientation of samples collected. As a result, techniques that are not rotationally and translationally invariant must account for this factor of variation directly in the model weights, which reduces the effective model capacity that can be dedicated to the structural variance of interest. Finally, in protein generation, nontrivial errors in local or global structure lead to completely implausible protein structures, which is a more stringent standard than for unconstrained image generation.

Described herein are embodiments of a new generative model. Introduced herein are embodiments of fully data-driven denoising diffusion probabilistic models (diffusion models) for protein structure, sequence, and rotamers that are able to generate highly realistic proteins across the full range of domains in, for example, the Protein DataBank (PDB). For comparison, protein macromolecules have approximately 100-1000× the atom count of the small molecules addressed by previous molecular generative models, and the full set of domain types in the PDB numbers in the hundreds, in contrast to the restricted single domain type addressed by previous structure generative modeling approaches. Embodiments of the models described herein are equivariant to rotations and translations by, for example, introducing invariant point attention (IPA) modules. In some embodiments, to handle the diffusion of rotational frames of reference that are involved in protein generation, a formulation is utilized that leverages an interpolation scheme well-suited to SO(3). In some embodiments, for discrete sequence generation, a masked autoregressive model is used that can be interpreted as a discrete diffusion model. In some embodiments, to allow for interactive structure generation, a compact set of constraints is introduced that the model conditions on to generate proteins. Embodiments of the diffusion models described herein are capable of generating high quality structures and sequences with nontrivial variety. As will be shown throughout, embodiments of the generative models described herein are capable of synthesizing physically plausible large protein structures and sequences across the full range of known protein domain types.

The generative techniques described herein provide various benefits over existing techniques for generating compounds. Previously, molecular modeling and design was performed on a computer using pre-existing software packages, such as Rosetta or other similar packages. The use of such packages typically involves specifying physics models, such as those describing interactions between atoms (e.g., Van der Waals forces, hydrogen bonding, etc.), modeling solvation, etc. The model specification may include various physical terms, where users define energy functions, determine weights, fit it to data, and then use such modeling to optimize the design of new protein structures and sequences.

While such previous packages have had some success in designing enzymes, generally, the amount of time to go from problem to problem is very large. The amount of time to design a structure typically requires running tens of thousands of optimization trajectories that may or may not actually converge. Further, when in a laboratory setting, the hit rate (e.g., the number of actual designs that work) is very low.

As another example challenge with existing techniques, existing protein modeling techniques are not invariant to rotation. For example, molecules are the same, whether or not they are rotated or translated in space. Some existing techniques represent proteins as coordinates in a 3D Cartesian space, but, if the machine learning models are explicitly trained on the exact coordinate position of such molecules, which are then rotated, then the output of the machine will be different.

Embodiments of the deep learning and machine learning techniques described herein circumvent the aforementioned issues in designing various types of proteins, and more generally in molecular design. As one example, the generative diffusion models described herein are rotation invariant, where the output will be the same, regardless of whether it is rotated or translated. For example, the generative models described herein are built to be invariant to rotations and translations, or to some extent, equivariant, where if the input is rotated, a rotated output is provided.

Using the generative protein diffusion techniques described herein, larger and more accurate and realistic structures of arbitrary length and size may be generated. As will be described in further detail below, embodiments of the design techniques described herein handle various aspects, such as rotational and translational invariance, as well as handling both local and global structure. For example, for a designed molecule to be realistic, it should be accurate globally (e.g., have the correct secondary structure regions, which refer to helices and beta strands), as well have the correct tertiary structures (e.g., appear folded, and as a globular-like protein). The proteins should also be locally accurate, where when evaluating a local portion of the predicted/generated protein structure, the local arrangement of the atoms is physically accurate as well. The generative techniques described herein provide such realistic protein structures. Further, the techniques described herein provide for controllably generating realistic protein structures. The techniques described herein are advantageous over existing techniques, such as physics-based software, which are unable to perform such controllable generation of structures.

Approach Overview

A protein is comprised of a sequence or chain of amino acids in a particular order (its primary structure). The linear chain of amino acids comprises two parts: a backbone; and side chain groups that come off of the backbone. The protein is a chain of amino acids, where the amino acids are linked to each other by peptide bonds to form the chain of amino acids. When the amino acids are linked together, there will be a chain of repeating carbon and nitrogen atoms (from the linked amino acids) that form a throughline through the protein. This chain of repeating carbon and nitrogen atoms is referred to in aggregate as the backbone of the protein structure. For each amino acid in the protein chain, the portion of an individual amino acid that comes off from the backbone (e.g., off the alpha carbon atom in the part of the individual amino acid that is defined as being part of the backbone) is referred to as a side chain. When linked in the protein chain, the individual amino acids are also referred to as residues.

Different proteins differ in the type, number, and/or sequence (order) of amino acids that are in the chain. Each protein is uniquely identified by the sequence of side chains in the protein.

A protein will ultimately have a certain 3D shape that results from the sequence of amino acids, which is a flexible chain, folding in on itself into a shape with some conformation (overall 3D spatial arrangement of atoms in the protein). The manner in which the folding of the chain occurs is based on the amino acids in the sequence (and for example, interaction forces between atoms in the chain). The final conformation that the chain is arranged into, or adopts, is the result of numerous folds. Two common types of folding patterns that are observed in portions or segments or stretches of the folded chain are alpha helices and beta sheets, which are referred to as the secondary structure of the protein. The beta sheet structures are groupings of beta strands, where the beta strands in a beta sheet may be oriented antiparallel to each other (antiparallel beta sheet) or parallel to each other (parallel beta sheet). The alpha helices and beta sheets are foldings of groups in the backbone portion of the protein, and do not rely or involve the side chains of the amino acids. The secondary structures (alpha helices and beta sheets) are connected via protein loops.

The overall 3D arrangement of the protein (chain of amino acids), which is the aggregate of the various folds of the chain, is referred to as the tertiary structure of the protein, which includes, for example, the spatial arrangement of the secondary structures relative to each other when folded.

In many cases, the shape of a protein will play a role in determining its function, with different domains of a protein associated with different functions. As described above, the shape of the protein is determined by the amino acid sequence (and its side chains). That is, the amino acid sequence determines the 3D shape and structure of the protein, where the structure of the protein in turn determines its function.

Thus, in some embodiments, designing a protein to perform a desired function involves: (1) determining a protein shape or tertiary structure (or backbone topology) that will perform the desired function, and (2) determining an amino acid sequence that will fold into the desired protein shape to yield the desired function. As will be described in further detail below, the generative models described herein are capable of generating the shape (structure) and amino acid sequence individually or jointly.

One example output of the protein diffusion model described herein is a sequence of amino acids that, if accurate, will adopt the predicted or desired structure when expressed in a laboratory setting. That is, there should be a correspondence, in a real-world setting, between the structure expressed in the laboratory setting from the amino acid sequence, and the structure that the amino acid sequence is predicted to fold into (and in some cases, for which the amino acid sequence was designed to adopt).

Protein Overview

The following are further details regarding proteins. Proteins are comprised of a repeating chain of atoms, called the backbone, with every fourth atom having an amino acid "side chain" of additional atoms known as a residue. The repeating pattern in the backbone is $N$–$C_\alpha$–$C$, and the side chain is attached to the $C_\alpha$ (alpha carbon) atom. Each $C_\alpha$ and its associated side chain is called a residue, and there are 20 different amino acids that can be attached to the $C_\alpha$. The 3D (three-dimensional) locations of all the atoms, together with the identities of the residues, fully describe the protein structure. There are several priors that constrain the distribution of the atom locations. First, there is a fixed bond length between atoms, which is what imposes the chain-like 3D structure. Second, the $C_\alpha$ can be interpreted as forming a canonical orientation frame with the N and C atoms. The amino acid attached to the $C_\alpha$ is constrained to have one attachment direction, and the positions of the atoms in the amino acid are physically constrained to vary only by rotation about sequential bonds; these rotations ("$\chi$ angles") are referred to as $\chi_1, \chi_2, \chi_3, \chi_4$. The atomic configurations of all 20 amino acids about the canonical orientation frame of their corresponding $C_\alpha$ are fully specified by some prefix of these four $\chi$ angles, since not all amino acids have the same number of atoms. As will be described in further detail below, in some embodiments, the aforementioned priors for such quantities are used in training. Experimentally- and theoretically-informed physical priors for such quantities may also be used in training. Example measurements of how well the models recover these priors from the data are provided below.

Summarizing the above, assuming an N-residue protein, one example goal of the techniques described herein is to learn a generative prior over the following variables:

$x_{C_\alpha}{}^i \in \mathbb{R}^3$ for $i \in \{1, \ldots, N\}$, the 3D coordinates of the $C_\alpha$ backbone atoms.

$q^i \in SO(3)$, the quaternion defining the global rotation of the canonical frame centered at $x_{C_\alpha}{}^i$. Using $q^i$ and $x_{C_\alpha}{}^i$ the positions of the associated N and C atoms can be recovered in closed form.

$r^i \in \{1, \ldots, 20\}$, the amino acid attached to the $i^{th}$ $C_\alpha$ atom.

$\chi_1{}^i, \chi_2{}^i, \chi_3{}^i, \chi_4{}^i \in [0, 2\pi)$, the four $\chi$ angles for the amino acid attached to the $i^{th}$ $C_\alpha$ atom. Note that some amino acids are made up of fewer atoms and thus have only a proper prefix of these angles.

In this example, $x_{C_\alpha}{}^i$ and $q^i$ are examples of variables or quantities relating to structure, $r^i$ is an example variable relating to sequence, and $\chi_1{}^i, \chi_2{}^i, \chi_3{}^i, \chi_4{}^i$ are example variables relating to rotamers.

In some embodiments, diffusion models are built for each type of variable, such as a structure diffusion model for diffusing the structure variables $x_{C_\alpha}{}^i$ and $q^i$, a sequence diffusion model for diffusing the sequence variable $r^i$, and a rotamer diffusion model for diffusing rotamer variables $\chi_1{}^i, \chi_2{}^i, \chi_3{}^i, \chi_4{}^i$.

In some embodiments, joint diffusion models are trained to jointly diffuse multiple types of variables concurrently (e.g., jointly diffuse various combinations of structure variables, sequence variables, and/or rotamer variables).

Described below are further embodiments of the diffusion process. Model adaptations to the non-canonicalized protein setting are also described below, followed by descriptions of two example ways in which the diffusion training process is adapted to the non-Euclidean (rotations for $q^i$ and $\chi$ angles) as well as discrete (sequence $r^i$) sub-problems. Described in further detail below are also examples of compact encoding schemes for constraints that are used in embodiments of conditional sampling of proteins. Embodiments of training and sampling procedures are also further described in detail below.

Protein Diffusion Model Overview

Diffusion models are a class of latent variable models that model the data generation process as iterative denoising of a random prior, with a specific parameterization of the approximate posterior distribution that can be interpreted as "diffusing" toward the fixed prior distribution. An example formulation is briefly described below. The data generation (reverse) process for a datapoint $x^0$ sampled from the data distribution $q(x^0)$ is defined recursively with a transition kernel $p_\theta$ and prior distribution $\pi$:

$$p_\theta(x^T) = \pi(x^T) p_\theta(x^0) = \int_{x^{1:T}} p_\theta(x^T) \Pi_{t=1}^{T} p_\theta(x^{t-1} | x^t) \tag{1}$$

The approximate posterior (distribution), referred to as the forward process, in the continuous case diffuses the datapoint $x^0$ toward the random prior:

$$q(x^{1:T} | x_0) = \Pi_{t=1}^{T} \mathcal{N}(x^t; \sqrt{1-\beta_t} x^{t-1}, \beta_t I) \tag{2}$$

where the $\beta_t$ are chosen according to a fixed variance schedule. In some embodiments, a neural network $\mu_\theta$ is used to parameterize the reverse transition kernel: $p_\theta(x^{t-1} | x^t) = \mathcal{N}(x^{t-1}; \mu_\theta(x^t, t), \sigma_t^2 I)$. In some embodiments, $\mu_\theta$ is obtained by minimizing the following variational bound during training:

$$L_{simple}(\theta) = \mathbb{E}_{t, x^0}[\mathcal{L}_{FAPE}(x^0, \mu_\theta(x^t, t))] \tag{3}$$

where $x^t$ is obtained by noising $x^0$ by q, and the rotationally invariant loss function $\mathcal{L}_{FAPE}$ is described below (e.g., in the section regarding Equivariant Diffusion Training). In some embodiments, sampling relies on the learned $\mu_\theta$ to execute a reverse process which maps a sample from the prior distribution to a sample from the data distribution.

There are various differences between the image and protein generation settings which impact the architecture of $\mu_\theta$ as well as the training and sampling algorithms. A first difference is described in the next section below, and a second difference in the section on Training and Sampling below.

Invariant Point Attention

As described above, one example difference between images and proteins is that proteins have no canonical orientation. As a result, in some embodiments, an equivariant transformer is used for embodiments of the denoising model $\mu_\theta$ described herein. In some embodiments, the model consumes as input an intermediate guess for the protein, $x^t$ and produces an estimate of the final ground truth structure $\hat{x}^0$. In some embodiments, the standard attention mechanism in the transformer is replaced with invariant point attention (IPA). In some embodiments, IPA partitions node query and value features into groups (e.g., of 3) and transforms them from the target node's reference frame into the source node's reference frame before computing both attention weights and the output of the attention mechanism. In this way, the output of the attention layer is invariant to the global orientation of the input protein, and thus the resulting corrections predicted by $\mu_\theta$ in the local coordinate frames of the $C_\alpha$'s are equivariant.

3D Representation of Protein Structure

In some embodiments, protein structure is represented as coordinates and coordinate frames. For example, in some embodiments, the protein representation is based on the above variables over which a generative prior is to be learned. For example, the protein is represented by the structure variables/quantities, sequence variables/quantities, and rotamer variables/quantities described above.

As described above, $x_{C_\alpha}{}^i$ and $q^i$ are structure variables that together describe a backbone topology (e.g., describes shape of a backbone when folded). Using $x_{C_\alpha}{}^i$ (the 3D coordinates of the $C_\alpha$ backbone atoms) and $q^i$ (the quaternion defining the global rotation of the canonical frame centered at $x_{C_\alpha}{}^i$), the positions of the associated N and C atoms can be recovered in closed form, thus producing the entire backbone and elided backbone atoms.

As described above, in some embodiments, a protein, which is a collection of atoms, is represented or modeled as a set of coordinates with corresponding coordinate frames for the represented backbone atoms (e.g., alpha carbon backbone atoms). This representation of coordinates and coordinate frames facilitates increased efficiency of training of the generative models described herein.

Another way to represent a protein is to model it entirely based on coordinates of all atoms. As one example, all the atom coordinates for the entire backbone are modeled and noised. This can be inefficient or resource intensive. For example, suppose a protein that is made up of 100 amino acids. Suppose that only the backbone is being considered (and not the side chains) in this example. In order to represent the backbone, 400-500 atoms may be needed. For example, each residue will in turn have a number of atoms, where there may be, for example, 4 atoms per residue. To generate a real(istic) protein backbone and have control over all of the atoms, there will be more than the number of residues—there will a number of atoms that is the product of the number of residues multiplied by the number of backbone atoms in each residue.

However, such models that are based on coordinates of all atoms may have suboptimal scaling with the size of the protein. With transformer-based models, there may be an $N^2$ or $N^3$ scaling, which would make it difficult to train such generative models on GPUs (whether a single GPU or distributed across multiple GPUs) when going from representing, for example, 100 atoms to 500 atoms.

In some embodiments, the use of coordinate frames is beneficial to effectively down sample the number of coordinates that are being modeled. By using coordinate frames, a subset of the backbone atoms are modeled (e.g., just the alpha carbon backbone atoms, without having to store the positions of the N and C atoms), where this representation is endowed with a coordinate frame. In this way, rather than 400-500 atoms needing to be represented, the protein backbone can now be represented with 100 coordinates (and corresponding coordinate frames).

For example, with respect to the backbone, for each residue, rather than representing all of the atoms in the residue that contribute to the backbone, the backbone portion of the residue is represented by a single starting atom for the residue (the alpha carbon atom, with its corresponding coordinate in 3D space) and a corresponding canonical coordinate frame for the residue. The positions of the remaining backbone atoms of the residue, if desired, can be inferred from the starting atom's coordinates and that atom's local coordinate frame (e.g., where the remaining backbone atoms are determined relative to the residue's starting atom's coordinates and the canonical coordinate frame). This form of compression using a starting atom's coordinates and a canonical frame is determined based on the types of bonds (e.g., planar bonds) that are present. In this way, given a canonical frame and a starting alpha carbon atom, the remainder of the backbone atoms of a residue are able to be inferred. That is, to describe the backbone structure (topology) of a protein, one representation includes recording, for each residue in the protein chain, a position (coordinates in 3D space) of the carbon alpha atom and a corresponding local canonical coordinate frame. This results in a reduced representation of the protein structure (backbone), where diffusion of the representation (that is based on residues) involves both handling diffusion of coordinates (of the positions of the alpha carbon atoms of the residue), as well as handling diffusion of the canonical coordinate frames (rotations) of the residues.

In various embodiments, other reduced representations of proteins may also be utilized (e.g., to reduce GPU memory utilization when scaling for larger and larger protein structures), with the diffusion techniques described herein variously adapted to accommodate diffusing or noising of the various components of those representations, as appropriate.

As described above, given positions and coordinate frames of alpha carbon atoms, the positions of all of the other atoms in the backbone that have been elided are inferred. The use of coordinate frames facilitates the generative models described herein to be trained in a much more efficient manner, which in turn allows the predictive results to be obtained by training using a smaller amount of hardware resources (e.g., allowing for training on a single graphics processing unit (GPU)). For example, as described above, transformer models may have suboptimal scaling, where it is challenging to predict larger and larger structures due to the, for example, $N^3$ scaling of memory usage on GPUs. The reduced protein structure representation described herein results in reduced memory usage on GPUs.

In some embodiments, the reduced representation described herein is used to perform structure prediction from a sequence to a structure. In some embodiments, in order to perform diffusion with such a reduced representation, a diffusion process is configured to handle rotations (of the coordinate frames that are included in the protein representation). In some embodiments, generative diffusion models are trained using such a reduced representation of protein structures.

As shown in this example, the protein structure has a multidimensional representation, such as a 3D representation. The following are embodiments of diffusing such a 3D representation to build a generative neural network for predicting protein structures. This includes diffusing 3D point clouds in 3D space, as well as diffusing coordinate frames.

Protein Diffusion Model Training and Sampling Architecture

The following are embodiments of building and using a diffusion model for protein structure and sequence prediction. In some embodiments, building of the diffusion model(s) includes training of a diffusion model (or models) for generating protein structures, sequences, and/or rotamers. In some embodiments, using the diffusion model includes a process of sampling the generative models.

FIG. 1 illustrates an embodiment of a system for predicting protein structure and sequence. In this example, platform 102 includes training engine 104 and sampling engine 106. The training engine is configured to train one or more protein diffusion models 108 using training data 110. Training the diffusion model includes noising the training data, where the diffusion model learns to recover the training data by reversing the noising according to a loss function. For example, the diffusion model parameters are tuned or updated to perform a reverse denoising process that minimizes a calculated loss (determined according to the loss function). As described above, one embodiment of a representation of a protein includes a structural component, a sequence component, and a rotamer component. In some embodiments, diffusion is performed for these components. For example, structure diffusion engine 112 is configured to perform structure diffusion, which in some embodiments includes coordinate diffusion and coordinate frame diffusion. Sequence diffusion engine 114 is configured to perform sequence diffusion. Rotamer diffusion engine 116 is configured to perform diffusion of torsion or chi angles of rotamers.

In some embodiments, diffusion of coordinate frames and diffusion of angles involves diffusion of rotations. In some embodiments, rotational diffusion engine 118 is configured to perform such diffusing of rotations. Further details regarding diffusion training, as well as rotational diffusion, are described below.

In some embodiments, there is one model each for structure, sequence, and rotamer diffusion. In other embodiments, models are trained to jointly diffuse structure and sequence concurrently (or any other combination of structure, sequence, and/or rotamers).

The sampling engine 106 is configured to use the trained protein diffusion model(s) 108 to generate or predict new protein structures and/or sequences. For example, sampled noise is provided as input to the diffusion model, where the trained diffusion model generates the new protein structure/sequence via the denoising that was learned during training.

In some embodiments, noise sampling engine 120 is configured to perform sampling of the noise.

In some embodiments, a protein diffusion model is trained to perform conditional protein generation, where the predicted protein structures/sequences are generated based on a set of input constraints. In some embodiments, the input constraints are received via front end interface 122. For example, a user such as a researcher may use their device 124 (e.g., laptop, desktop, mobile phone, tablet, etc.) to communicate with platform 102 via network 126 (e.g., the Internet, or an intranet). In some embodiments, the user is able to provide constraints via an interface supported by front end 122 (and displayed on their device). Examples of user interfaces for providing constraints are described in further detail below. The constraints received via the front end are processed by constraint engine 128, which for example provides them to sampling engine 106 for use in sampling the trained protein diffusion models. In this example, quality control engine 130 is configured to perform quality checks on predictions made by the sampled protein diffusion model(s). Further details regarding quality checks are described below.

Figure 2:
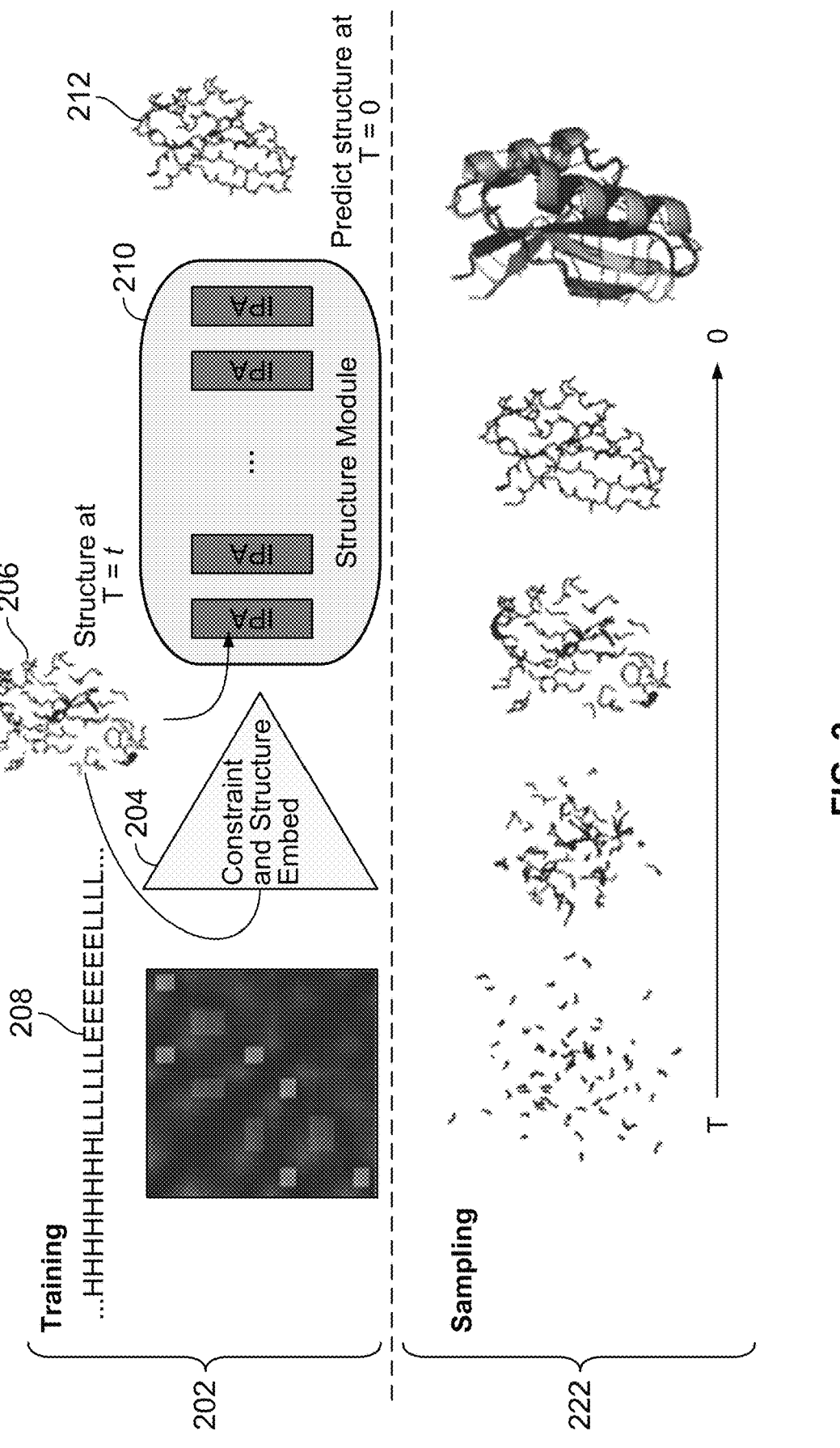
FIG. 2 illustrates an embodiment of a training and sampling architecture for generative protein design.

FIG. 2 illustrates an embodiment of a training and sampling architecture for generative protein design. An embodiment of a training process is shown at 202. In some embodiments, training process 202 is executed by training engine 104 of platform 102. An embodiment of a sampling process is shown at 222. In some embodiments, the sampling process 222 is executed by sampling engine 106 of platform 102.

During training time (202), in this example, the noised structure 206 (at some time step t) is shown to be inputted to the structure module 210, separately from the embedded constraints. In some embodiments, the noised structure 206 is also sent through a primary network (constraint embed module 204), which also embeds constraints 208, where the combined noised structure with the embedded constraints is provided as input to the structure module 210. In some embodiments, the structure module is trained to refine the noised structure, which includes correcting or de-noising the noised structure. That is, in some embodiments, a noised structure and feature embeddings are provided as input to the structure module 210, which provides as output a refined structure 212 (e.g., prediction of what the original structure is after de-noising the input noised structure).

In some embodiments, the constraint and structure embed module 204 that embeds the noised structure and constraints, and the structure module 210 that takes those embeddings along with the current noised structure to refine the noised structure based on the feature embeddings are two components of the overall generative model, where the entirety of the architecture is trained end-to-end (where those two components are trained together, for example).

In some embodiments, during sampling 222 of the trained diffusion model, a noised structure and a set of constraints are provided as input, and the diffusion process is run in reverse, where the model predicts a corresponding refined structure.

In some embodiments, the neural network model is configured to evaluate the combination of the constraints, as well as the noised structure to infer (what the neural network model believes to be) a ground truth structure. As one example, suppose that the process is in a regime with a very high t, where there is effectively no information about what the underlying structure (ground truth) is, and where the underlying structure has effectively been erased due to noising to a random starting point, which is one example of what occurs at the start of sampling—that is, there is little information about what the underlying structure is, as it is mostly random. In some embodiments, the denoising during sampling time effectively progresses from high time t, to low time t, which for example is the opposite of the progression of the diffusion process.

In some embodiments, the network makes a prediction at each time step. For example, at high t, the denoising is just starting, and the prediction is in its early stages. As time progresses, the network predicts what features or structure are present. This includes making correlated predictions. When the network, for later stages, reaches a local minimum (e.g., in the overall space of structures), the network begins to refine the structure (local optimization). In some embodiments, the neural network prediction is based on what ground truth it has been trained on.

In some embodiments, the network utilizes the constraints as information to guide its denoising, to determine, for example, that a region should be helical, or that another region should be in beta space, etc. That is, the model considers both the input noise and the conditioning information.

Thus, using the generative techniques described herein, proteins are generated that adhere to constraints.

Training Data

In some embodiments, the training data (also referred to herein as ground truth) includes protein structure data. As one example, the structure data is obtained from a database such as the Protein Data Bank. In various embodiments, the structure data includes crystal structure data, cryo-EM (cryo-electron microscopy) structures, NMR (Nuclear Magnetic Resonance) structures, as well as other experimentally derived structures. As one example, the structure data from the Protein Data Bank is received as ordered files of 3D point clouds. In some embodiments, platform 102 is configured to process the 3D point cloud data to generate the structural, sequence, and rotamer representations described above. For example, to determine a reduced structural representation, platform 102 is configured to identify the alpha carbon backbone atoms, and for each of the alpha carbon backbone atoms, determine a position (coordinates) and corresponding rotational frame of reference. The reduced protein representation is then stored as training data (e.g., in training data store 110) for use in training the protein diffusion models.

In some embodiments, in addition to using crystal structure data from the Protein Data Bank in the training data, predicted structures are also included. For example, predicted structures generated from sources such as Alphafold or other structure prediction engines are used to bootstrap the available amount of training data. In some embodiments, filtering is performed to obtain high confidence Alphafold predictions. Training on such high confidence predictions is then used to boost performance of the diffusion model.

For illustrative purposes, protein domains are considered herein, which include globular regions of proteins that are able to fold on their own. The techniques described herein may be extended to full chains and complexes.

The following are embodiments of training generative models for predicting protein structures. A generative model is trained on the training data described above.

In some embodiments, given a structure representation of coordinates and coordinate frames, the diffusion process includes diffusing coordinates, as well as diffusion rotations (e.g., diffusing of coordinate frames). Sequence and rotamer diffusion training are also performed. Joint diffusion of structure, sequence, and/or rotamers may also be performed.

Training

The following is an overview of the training process for training a generative model for predicting protein structure and/or sequence. For example, ground truth is noised. A generative model is trained to denoise to the ground truth. The noising is performed on a schedule, where the extent to which noising is performed is a function of a variable, such as time. For example, at a time t, the ground truth structure has been taken and noised. The noised ground truth structure is sent into a network. In some embodiments, constraints and other conditioning information are also provided as input to the network. The network is then tasked with denoising the noised structure. In some embodiments, the denoising is performed to predict the ground truth. As another example, the denoising is performed to predict the actual noise.

For example, a structure is received. The structure is noised. The noised structure is sent, along with a set of constraints, as an input to the network (e.g., structure module 210). The network is responsible for learning how to map from the noised input structure to a refined output structure. In some embodiments, during training, the time is randomly sampled, which can be either sampled in a discrete or continuous manner. As one example of discrete time sampling, the time step is sampled uniformly at random. If the time is a higher or larger value, then the extent of noising is greater. For smaller time, the extent of noising is smaller. In this example, the model is taught to perform time dependent denoising. The model is also conditioned on time as well.

As one example, suppose a ground truth structure (e.g., from the training data target distribution). A random sample is taken from a noise distribution. Interpolation is performed between the ground truth structure and the random sample to obtain an input to the model.

The generative model being trained is responsible for denoising the input structure (which, in the middle of the schedule, is a structure that is interpolated to be between ground truth and the random sample).

The manner in which the interpolation is performed (in order to progressively noise the ground truth until it becomes the random sample from the noise distribution) is based in part on how the structure is represented. As described above, in one embodiment, the protein structure is represented as a selected subset of backbone atoms (e.g., alpha carbon atoms), where each selected backbone atom is associated with a corresponding coordinate and a corresponding orientation frame. The diffusion model described herein is invariant to rotations using the techniques described herein.

As described above, in some embodiments, a protein structure is represented as a set of coordinates (of a subset of the atoms in the structure), as well as corresponding coordinate frames. The following are embodiments of noising (1) the coordinates of the backbone atoms, and (2) the corresponding coordinate frames when performing structure diffusion. Embodiments of sequence diffusion are also described in further detail below. Embodiments of rotamer diffusion are also described in further detail below. Embodiments of diffusing rotations (which is performed for both structure diffusion (for the coordinate frames) and for rotamer diffusion) are also described in further detail below.

Coordinate Diffusion (Noising Coordinates)

In some embodiments, the starting point of the set of coordinates is the ground truth set of coordinates for the atoms (in 3D space, represented for example as a point cloud) in the ground truth protein structure (that the generative model is being trained on). As described above, as part of the training process, the ground truth is progressively noised over a set of time steps. This includes interpolating between the ground truth and a selected noise (cloud). For example, at low time points, the noise is scaled to near zero and added to the ground truth, which is scaled near one. At high time t, the ground truth is scaled to zero, which is then added to noise, where the coefficient or weight of the noise is scaled to one. As one example, the schedule of the interpolation (to noise the ground truth) includes performing linear interpolation. As one example, a noise mask is applied to ground truth. One or both of the noise mask and the ground truth may be weighted or scaled as part of the noising schedule. That is, one or both of the noise mask and the ground truth may be scaled up or down, where at the beginning of the process, there is ground truth and nearly no noise, while at the other end of the schedule, there is primarily noise and little ground truth.

As one example, suppose a 3D Gaussian in space, where the Gaussian is scaled such that if the Gaussian were overlaid in the structure, there is a significant amount of overlap. This is in contrast to having a small Gaussian and a large structure, where if interpolation toward a small Gaussian is performed, a large amount of information about the structure is preserved.

In some embodiments, the Gaussian used to determine the noise is at a scale similar to that of the coordinates. In some embodiments, scaling is performed that is a function of the radius of gyration of the protein. This results in an entity that can also be titrated.

In some embodiments, the size of the noise cloud is adjusted to change or influence the size of the desired domain.

As one example, each alpha carbon backbone atom in the reduced representation of the protein structure is associated with a corresponding coordinate position in 3D space. For example, the atom is associated with a corresponding three-dimensional vector that indicates its X, Y, Z position.

In some embodiments, noising the coordinate includes noising or changing its position. In some embodiments, noising the coordinate of the atom includes interpolating toward a 3D Gaussian distribution that is scaled.

In some embodiments, noising or diffusing the coordinate of the atom includes diffusing or noising the explicit 3D Cartesian coordinate toward a coordinate sampled from a scaled 3D Gaussian. Put another way, in some embodiments, diffusing a coordinate in 3D Cartesian space is performed by diffusing it toward a random scaled 3D Gaussian, or a sample from a random scaled 3D Gaussian distribution (or any other distribution over points in 3D, or the same dimensions as the coordinates). The coordinates may be diffused towards samples drawn from other 3D distributions as well.

As described above, in some embodiments, the ground truth data for a protein (e.g., from the PDB) includes a 3D point cloud, where for every atom (or subset of atoms included in the reduced representation), there is a corresponding three-dimensional coordinate. In some embodiments, the noising performed by the diffusion process includes diffusing the ground truth 3D point cloud towards a randomly selected cloud of coordinates. In some embodiments, there is also a random coordinate frame at each of the coordinates in the cloud of coordinates (corresponding, for example, to coordinates of alpha carbon atoms). Further embodiments of diffusing from ground truth coordinate frames to random coordinate frames are described below.

Equivariant Diffusion Training (Noising Coordinate Frames and Rotamer Angles)

Equivariant Diffusion Model

Embodiments of the diffusion models described herein are equivariant. For example, embodiments of the equivariant diffusion models described herein are rotationally and translationally equivariant diffusion models. With an equivariant diffusion model, given some starting noise that yields an output, providing rotated starting noise will yield the same output, rotated.

In some embodiments, invariant point attention (IPA) is used to decode structure, allowing the model to be kept rotationally equivariant, end-to-end. In some embodiments, invariant point attention is used to decode structures in a manner that is rotationally and translationally equivariant.

With embodiments of a diffusion setup defined as described above, and a model architecture such as that shown in FIG. 2, the following are examples of techniques for addressing specific challenges of the training setup in an equivariant setting.

The following are embodiments of building a deep diffusion model that is configured to handle rotations (e.g., of quaternions, coordinate frames, angles, etc.). This includes embodiments of a diffusion model that handles noising or interpolating between ground truth and random rotations. In some embodiments, diffusion is performed toward a uniform random (or any other appropriate prior distribution).

Diffusing Rotations

Unlike coordinates, the rotation variables $q^i$ (structure variable) and $\chi_{1:4}^i$ (rotamer angle variable) described above do not live on Euclidean manifolds with flat geometry; therefore during training and sampling they cannot be diffused towards their prior distribution simply by randomly scaling and perturbing their encoding as is the case with coordinates.

In some cases, to address such limitations, diffusion frameworks are extended to compact Riemannian manifolds, which in turn may be adapted to modeling rotational diffusion as the repeated application of a heat kernel on a torus. A more efficient technique is described herein that is effective in practice. In some embodiments, for a prior distribution $\pi_q$ for rotations, a uniformly random rotation in SO(3) is used. Next, instead of diffusing from $x^0$ towards $\pi_q$ with Brownian motion and thus modifying the reverse process to use the Euler-Maruyama sampler, interpolation is performed from $x^0$ to a sample $\epsilon \sim \pi_q$ based on the schedule of variances (see, for example, Table 1 below). Various ways to interpolate between rotations may be utilized; in some embodiments, spherical linear interpolation is used (SLERP (x, y, α), where interpolation is performed from x to y by a factor of $\alpha \in [0,1]$). These design choices have the desired effect of exposing the network to a similar distribution of random rotations both at training and test time, which is also reflected in practice in experiments. Other approaches can also be used.

As described above, when using a protein representation that includes coordinate frames/quaternions, interpolation is performed for noising/denoising such rotations. As one example, spherical linear interpolation (SLERP) is used to facilitate smoothly rotating between two rotations. For example, SLERP facilitates determining intermediary rotations, in 3D space, between a starting orientation and an ending orientation.

As one example of SLERP, suppose that a rotation is represented as being two points on a sphere (e.g., four-dimensional sphere associated with quaternions), corresponding to two coordinate frames of interest. SLERP facilitates interpolation between a geodesic on a sphere. For example, SLERP facilitates interpolation between the two rotations. The interpolation between the two points on the sphere may progress on either a short path or a long path.

In some embodiments, the interpolation that is selected is the short rotation path (to rotate from a starting orientation to an ending orientation). The long rotation path may also be selected in other embodiments. In some embodiments, the selected type of rotation path is consistently utilized.

As described above, in some embodiments, the starting and ending points are represented as coordinate frames or quaternions, where a coordinate frame dictates, at least in part, information about the relative atom positions of the elided atoms on the backbone.

For example, suppose a ground truth (in a starting orientation) and a random sample (in an ending orientation). In some embodiments, the noise samples (that the ground truth is diffused towards) are drawn from prior distributions such as uniform distributions, Gaussian distributions, etc. The diffusion process, during training time, is configured to interpolate between the starting and ending orientation/rotation points, including generating intermediate orientations along the path of rotation (e.g., SLERP) between the starting and ending points.

At low t during training, the various portions of the protein (backbone) are still at or close to their ground truth starting rotations. At high t, the diffusion process has rotated the various portions of the protein to be far away from their starting rotations, and closer to the randomly selected rotations/coordinate frames.

When the diffusion process is close to low t, there is still a large amount of information about what the ground truth coordinate frame or quaternion is. In a middle region, it may be more difficult to determine what the starting coordinate frame was. At high t, there is little information about what the starting coordinate frame was.

As shown above, in some embodiments of the structure diffusion process (noising of ground truth), noising of coordinate frames is performed. As one example, suppose N points in space (e.g., coordinates) that are to be noised. Gaussian interpolation may be used to perform the diffusion noising on these N points in space. Suppose also that each and every single point has a coordinate frame. The coordinate frames are also being noised, for example using the interpolation techniques described above.

Existing diffusion techniques include the use of Gaussian distributions. The use of Gaussian distributions provides properties that facilitate modeling diffusion as having a connection to probabilistic graphical models. For example, diffusion models are a form of probabilistic graphical models, where diffusion models with neural networks may be used to mimic a probabilistic graphical model framework. That is, the use of Gaussian distributions as a type of prior distribution allows for the use of certain frameworks.

In some embodiments, diffusion of coordinate frames, which are associated with rotations and quaternions, is formulated as diffusion on a sphere. For example, quaternions may be considered as a four-dimensional sphere, and the diffusion process is performed along the surface of this sphere.

In some embodiments, a uniform distribution on SO(3) is used as the distribution on the space of rotations. In the diffusion techniques described herein, diffusion is performed along a surface of a sphere, where a random point is sampled on the sphere. The diffusion process involves determining intermediate interpolations between the ground truth coordinate frame and the randomly sampled coordinate frame.

The interpolation is performed such that the intermediate interpolations are along the surface of the sphere. In some embodiments, spherical linear interpolation is used to perform the interpolation. The use of such interpolation allows for the creation of equivariant diffusion models on coordinate frames.

The aforementioned use of the uniform distribution, as well as interpolation such as spherical linear interpolation, result in more empirically effective results in practice.

The following are further embodiments of noising (diffusing) coordinate frames. As described above, as part of structure diffusion, in addition to noising of atom coordinates, coordinate frames are also noised as part of the noising process.

As one example, suppose a coordinate frame, where there are, for example, three axes of coordinates. The three axes represent an orientation of the coordinate frame. As one example, a uniform random coordinate frame is sampled. In some embodiments, noising of the coordinate frame involves interpolating, over multiple steps, from the ground truth coordinate frame to the uniform randomly sampled coordinate frame.

This is in contrast to diffusing in the image space, where for single values of pixels, interpolation involves addition (e.g., upweighting one, down-weighting another, and adding them together for smooth interpolation).

In the context of coordinate frames, as described above, in some embodiments, SLERP interpolation is performed to preserve meaningful information regarding geometry. The use of SLERP allows for interpolation of 3D rotation (rather than, for example, 1D scalar interpolation in the context of image pixel values).

As described above, the diffusion of canonical coordinate frames includes diffusing to a random rotation, where as one example, the diffusing (which is done over time, according to a schedule), is performed using SLERP to interpolate between two coordinate frames (the ground truth coordinate frame and the random coordinate frame drawn from the noise prior).

As one example, a sample coordinate frame is drawn from a distribution. For example, a uniform random rotation is sampled. As one example, a random axis in a random angle is sampled, which corresponds to a uniform random rotation. (This type of sampling during training is similar but separate from sampling from the generative model, described in further detail below, where sampling from a learned distribution is performed, where instead of drawing a scalar or drawing a rotation, a protein structure is drawn).

As another example, a ground truth coordinate frame is received from the representation of the ground truth protein structure. The ground truth coordinate frame, as one example, includes 3 axes (X-axis, Y-axis, and Z-axis), where the axes are in a ground truth orientation. A random coordinate frame is sampled, where the three axes are in a different, randomly selected orientation. Interpolation is performed to rotate the ground truth coordinate frame towards the random coordinate frame. The interpolation is performed as a function of time, so that the coordinate frame is progressively rotated from the starting coordinate frame orientation (what was specified in the ground truth), to the ending coordinate frame orientation (which was sampled). The interpolation (also referred to as a type of diffusion) provides, for example, an intermediary orientation of the coordinate frame that is between the starting point and the endpoint orientations of the coordinate frame.

At lower time t, there remains some information about the ground truth coordinate frame. That is, during the training process, the diffusion process is aware (based on the time t) the extent to which the coordinate frame should be noised. That is, if the coordinate frame is currently oriented in a certain manner, and the time is small, then the orientation is unlikely to be dramatically different from the ground truth— it is more likely that there is a relatively smaller delta or deviation in orientation or rotation of the coordinate frame.

The interpolation between the starting and ending orientations of the coordinate frame may proceed along a longer path or a shorter path. Either the longer rotation path or the shorter rotation path may be selected. In some embodiments, for consistency, the same type of rotation path is selected for the diffusion process as part of training the generative model.

As described above, the use of coordinate frames in representing protein structures provides efficiency benefits. For example, in some representations, coordinate frames or quaternions are not used in the protein structure representation, and all coordinates are noised. In comparison to the reduced representation described herein involving coordinate frames, more coordinates will have to be noised during the diffusion process. For example, the use of coordinate frames allows for the protein (backbone) to be represented using a fraction of the coordinates (e.g., 4× fewer coordinates), along with a coordinate frame for each coordinate. With the introduction of coordinate frames, embodiments of the diffusion process include not only noising of the subset of coordinates, but also handle diffusion of the coordinate frames in a memory-efficient manner.

That is, fewer coordinates are needed to be modeled for the protein, as they are being represented in part using coordinate frames, which allows for downsampling the number of coordinates that need to be represented (to only include, for example, the alpha carbon atoms), which in turn provides various efficiency benefits for training the generative models described herein. For example, every atom has not only a coordinate (position in 3D space), but also a corresponding coordinate frame. This allows for a representation of a protein that does not require modeling the coordinates of every single backbone atom (rather, just the alpha carbon atoms). Such a reduced representation allows for less memory to be needed to perform model training.

With respect to rotamers, chi angles are diffused in some embodiments. As a simplified example, for illustrative purposes, suppose a ring, where the diffusion is required to occur on the ring (e.g., analogous to a clock face, with the minute hand having to be on the ring of the clock). This is performed, in some embodiments, in the case of rotamers. The angle of the minute hand relative to some position may be determined. Suppose that diffusion of the angle of the minute hand is to be performed. A random angle (e.g., between 0 and 27r) is sampled. As part of the diffusion process, interpolation is then performed between the ground truth angle and the randomly sampled angle to generate intermediate interpolations, where the intermediate interpolations are interpolated angles of the minute hand between the ground truth angle and the randomly sampled angle (where the randomly sampled angle can be considered as a type of random noise that the target is diffused (noised) toward).

Rotational Invariance

In some embodiments, training $\mu_\theta$ involves a loss function that can stably account for errors in all of the predictions of the generative model. Small errors in the rotation prediction $q^i$ for a given $C_\alpha$ atom can cause its associated rotamer to clash with other rotamers. In some embodiments, frame-aligned point error (FAPE) loss is used. In some embodiments, FAPE penalizes errors in rotation by computing the squared distance between the $N_d(r_i)$ atoms in a neighborhood of radius d around each residue $r_i$ in the predicted structure, but only after aligning the predicted structure to the ground truth structure to match both the translation and rotational frames at each residue in turn. As one example, in total there are $\Sigma_{i=1}^{N} N_d(r_i)$ distance measurements, which are averaged together to yield the final FAPE loss. Because coordinate frames are aligned when computing loss, the training procedure is invariant to the orientation of protein structures in the dataset.

In some embodiments, the training is performed according to one or more objectives. As described above, one embodiment of an objective is a rotationally invariant loss function that performs an alignment of the predicted structure with the ground truth, and then incurs a loss to determine how close the predicted structure is to the ground truth. In other embodiments, alignment is not performed, and a distance (calculated loss) between the predicted output (also referred to herein as the "refined" output) and the ground truth is determined. Multiple objectives (e.g., hybrids of combinations of objectives) may be considered when comparing the predicted output (at various time steps) against the ground truth. The weights or parameters of structure module 210 are then updated to, for example, minimize calculated loss.

Discrete Sequence Diffusion

In some embodiments, the protein design platform is configured to perform sequence diffusion. In some embodiments, a masked autoregressive formulation is used to generate the sequences on top of the backbones. In some embodiments, this is equivalent to diffusion with a uniform random absorbing state. As one concrete example, the model is trained by random masking a fraction of the residues, where the fraction is linearly interpolated in [0,1] during training as a function of t. In some embodiments, at test time, the reverse process is run by masking all residues at t=T, and iteratively sampling from the model and masking a smaller fraction at each iteration as t approaches 0.

Rotamer Diffusion

In some embodiments rotamer diffusion is performed to determine the orientation of side chains that hang off of the backbone. In some embodiments, rotamer diffusion, which involves diffusing rotations, is also performed using embodiments of the interpolation described above, with respect to the rotamer variables $\chi_{1:4}^i$. Further details regarding diffusing of rotations for rotamer diffusion are described above with respect to diffusing rotations.

Constraints

In addition to encoding a manifold on which relevant inverse problems can be solved, a benefit of a generative model for protein structures and sequences as described herein is in allowing a researcher to specify simple, compact conditioning information about what they want to see, sample many valid protein configurations based on that, and iterate on the conditioning information until the desired results are obtained. While one example of such constraint specification is described herein for illustrative purposes, the model is agnostic to this choice, and other constraint specifications may be utilized.

A protein's residues can be divided into contiguous, adjacent blocks based on the secondary structure of the block: either a helix, a beta sheet, or a loop. Furthermore, each pair of helix or beta sheet blocks can be considered to be adjacent or non-adjacent based on whether or not their closest atoms are within some distance threshold. For paired beta sheets, besides adjacency, whether the sheets are parallel or anti-parallel to each other may also be specified. One way to compactly describe a protein is by specifying a number of residues N, then a tuple of numbers of length B adding up to N which indicate the block sizes, then a block secondary structure assignment {helix, sheet, loop}$^B$, and finally a symmetric block adjacency matrix in $\{0,1\}^{B \times B}$ together with a parallel/anti-parallel prior on each beta sheet pairing. This specification is highly compact; for many proteins of interest B is between 10 and 20. At the same time, the specification does not overly constrain the model to produce just one structure; it allows for nontrivial variation as seen in below (e.g., in Context-Free Generation, further details of which are described below). Further details and examples of providing such constraints are described below.

Triangular Self-Attention

In some embodiments, these constraints are provided to the prediction model $\mu_\theta$ as node and edge features. In some embodiments, before being passed to $\mu_\theta$, they are embedded via an invariant transformer. In some embodiments, the transformer performs attention not just between pairs of blocks but across all triplets of blocks. This is important for the protein modeling problem because blocks have non-trivial interactions beyond the pair level; for example, cycles in the block adjacency graph corresponding to beta sheet pairings must have length at least four, so it is important for the model to be able to easily learn features that reject cliques of beta sheets of size three.

The following are further embodiments of embedding constraints. Various techniques may be utilized to embed constraints. As described above, as one example, attention is used to embed constraints.

Referring to the example architecture of FIG. 2, in some embodiments, the network architecture includes a constraint and structure embed module 204. In some embodiments, the constraint and structure embed module is implemented as a network that reasons about a current noised structure (e.g., ground truth structure that has been noised or diffused as of some current time step T=t) as well as the constraints. Example implementations of the constraint and embed module include a U-Net, a U-Net with attention, a variance on transformer architectures, a triangle transformer architecture, etc. The network embeds the constraints and the structure and learns features about what the refined structure 212 should look like. In some embodiments, the IPA structure module 210 is configured to take those features and map those features to an actual structure.

In the example of FIG. 2, the structure is provided as input to the constraint and structure embedding network, and is also provided as input to the structure module. In some embodiments, the structure module 210 is configured to take the current noised structure 206 as input, as well as the features that have been learned about how to update that structure, and makes those updates. In some embodiments, the model is equivariant, making the process more optimal. In some embodiments, the structure module is equivariant to rotation, such that if the structure is rotated, and the features were kept the same, the same output, but rotated, is provided.

Sampling

As described above, in some embodiments, during training, a ground truth is received. This includes a ground truth representation of a protein structure. Noise is sampled. For example, Gaussian noise is sampled or a random coordinate frame or angle is sampled. Interpolation is performed between the ground truth and the noise in order to obtain a noised structure that the generative model is trained to de-noise.

After the generative model is trained, requests are made to the generative model to create a realistic protein structure and/or sequence (according to the user's constraints as well). In some embodiments, in order to generate the protein structure and/or sequence, sampling of the diffusion model is performed. For example, during sampling time, a random sample from the learned noise distribution is drawn. This sampled noise is provided as input to the generative model. Starting from the sampled random noise (e.g., noised structure), the generative model iteratively predicts and interpolates back (as the predicting is performed) towards a realistic protein structure. For example, the reverse of the diffusion process is run to generate or synthesize a new protein structure or sequence from the input noise (and constraints).

As one example of performing sampling for generating realistic protein structure, the process starts from a random example from a prior distribution, such as a random scaled Gaussian, with uniform random rotations for each coordinate frame. At each step, there is a prediction of the denoised ground truth. In some embodiments, interpolation is performed, where steps are taken toward the prediction. While this may be noisy, steps are taken in the direction of the predicted refined structure, resulting in a progressive refinement.

In some embodiments, for rotations (e.g., of denoising coordinate frames and chi-angles) the interpolation is performed using spherical linear interpolation, to handle rotations of coordinate frames or quaternions or angles, as described above.

As described above, in some embodiments, performing sampling includes specifying constraints and drawing a random example/sample. The selected random example (from the distribution) and the constraints are passed through the model. The drawn random example is passed through the model for each time step, and at the end of the sampling process, a realistic protein structure is generated. During sampling, there is no ground truth. In some embodiments, for the generative model, the generative model has captured a learned distribution, where the distribution is over protein structure.

Further Embodiments of Training and Sampling

The following are embodiments of overall design choices.

Referring again to FIG. 2, FIG. 2 illustrates an embodiment of a protein diffusion model. In the example of FIG. 2, coarse constraints 208 are specified to the model—the secondary structure (helix, loop, sheet) of the protein and "block" adjacency information (including beta strand pairing). In some embodiments, the model samples backbones that satisfy the input constraints.

In some embodiments, the generative model conditions on a compact specification of constraints for a given protein, as described above. In some embodiments, these constraints are embedded using a transformer with triangular self-attention (e.g., constraint and structure embed 204) to produce feature embeddings which are processed using Invariant Point Attention (e.g., in structure module 210) to produce updates to the translations, rotations, and residues in the local coordinate frames of the $C_\alpha$ atoms. During training, these updates are used to compute rotationally-invariant losses. During sampling, these updates are used to take steps toward the final structure.

Table 1 summarizes for each variable the prior distribution, embodiments of approaches used to interpolate between the data distribution and the noise distribution during training, as well as embodiments of techniques for taking a step at sampling time. Table 1 above provides summaries for the two processes: (1) training; and (2) sampling.

In some embodiments, to generate a structure, a starting point is sampled from the prior distribution corresponding to $t=T$, and the update described in the "Sample Step" column in Table 1 is iteravely applied for all variables for $t \in \{T, \ldots, 1\}$. In this example, the sample of the generative model is taken to be the value at $t=0$.

TABLE 1

| | Example Diffusion Process Hyperparameters | | |
|---|---|---|---|
| Variable | Prior Distribution ($\pi$) | Training Noising (step t) | Sample Step (step t) |
| $x_{C_a}^i$ | $\mathcal{N}(0, 1)$ | Diffusion with $x_0$ prediction and cosine schedule | |
| $q^i$ | Uniform(SO(3)) | $q_t^i = \text{SLERP}(q_0^i, q_T^i, t/T)$ | $q_{t-1}^i = \text{SLERP}(q_t^i, \hat{q}_0^i, 1/t)$ |
| $\chi_{1:4}^i$ | Uniform($0, 2\pi$) | $\chi_t^i = \text{SLERP}(\chi_0, \chi_T, t/T)$ | $\chi_{t-1}^i = \text{SLERP}(\chi_t^i, \hat{\chi}_0^i, 1/t)$ |
| $r^i$ | Fully Masked | Mask each residue with probability t/T; predict and incur loss on masked. | Mask each residue with probability t/T; predict masked. |

Example Implementation

As one example, the diffusion models described herein are trained on X-ray crystal structure data of CATH 4.2 S95 domains from the Protein Data Bank (PDB). In this example, domains are separated into train and test sets based on CATH topology classes, splitting classes into ~95% and 5%, respectively (1374 and 78 classes, 53414 and 4372 domains each). This largely eliminates sequence and structural redundancy between the datasets, which facilitates evaluation of the approach's ability to generalize.

Constraint Embedding Model

Suppose an N residue protein with C blocks, which produce C×C pairwise adjacency constraints. As one example, these constraints are embedded via a transformer (e.g., constraint and structure embed 204) over the C nodes using triangular self-attention. In this example, this transformer has 8 layers, each with 8 heads and 64 features, with weight sharing between the 8 layers. As one example, the secondary structure information is encoded via a 1D BeRT architecture with 8 layers, 8 heads, and 8 features each. In this example, the constraint network produces C embedding vectors, and each residue in the diffusion model described below conditions on both the constraint embedding vector from its block as well as the secondary structure embedding vector as additional node features.

Diffusion Model $\mu_\theta$

In some embodiments, the diffusion model conditions on the output of the constraint network and the current structure and produces a guess or prediction for the final structure configuration. As one example, the model (e.g., structure module 210) includes 10 layers of IPA, each with 8 heads and 128 features each, and weights are shared across all 10 layers. In some embodiments, when predicting $\hat{x}_{C_\alpha}$ and $\hat{q}$, each internal layer of IPA produces an intermediate guess which is applied to the structure before computing the next round of IPA weights.

Training and Sampling

In an example embodiment, during training, the prior distributions and noising procedures described in Table 1 are used, sampling t uniformly at random in [1,1000]. In one embodiment, the Adam optimizer is used with learning rate $10^{-4}$ and a cosine learning rate decay schedule. As one example implementation, the models are trained on single K80 and V100 GPUs on Google Cloud.

In some cases, higher quality results may be obtained without adding noise during sampling, so the variation in samples comes from the variation in the samples from the prior at $t=T$. As one example, $T=1000$ diffusion steps are used during both training and sampling. In some embodiments, three separate models are used for structure, sequence, and rotamer diffusion; in other embodiments, the models are combined into one and the diffusion process executed in parallel for all variables.

The following are embodiments of applications of the protein diffusion model described herein, including context-free generation, protein completion, and sequence design and rotamer repacking. In some cases, there is no post-processing on the samples produced; all results are based on the raw output of the diffusion process at $T=0$.

Example Design Tasks Supported by Protein Diffusion Models

Embodiments of the generative model described herein are used to support or perform various protein design tasks. Embodiments of such tasks facilitated by the protein diffusion models described herein are described in further detail below.

Context-Free Arbitrary Backbone Structure Generation

One example limitation of existing techniques is that they are less capable of performing generation of backbones of arbitrary length. Existing techniques may be more limited to specific design tasks, such as loop engineering, a type of in-painting task where only a portion of the structure is re-engineered.

Embodiments of the generative modeling described herein are capable of conditional generation of backbones, as well as generating arbitrarily large structures of arbitrary size that are also highly accurate at a local level (e.g., with bond lengths, bond angles, backbone torsions, etc. that adhere to biophysical ground truth) that are conditioned on constraints. This includes taking constraints (e.g., description or constraints on a desired structure) as input, and generating realistic backbone structures (of how the chain of repeating carbon and nitrogen atoms will fold, without side chains).

The following are embodiments and assessments of performing the task of synthesizing accurate 3D designs of proteins, relying just on the compact specification of the protein. This task is difficult because the model must produce a physically plausible structure that also respects the coarsely-defined adjacency priors. To assess the degree of generalization of the algorithm on native backbones from the test set, which have CATH-defined topologies not seen by the model during training, four test case backbones that span the major CATH classes are selected—all alpha, alpha-beta, and all-beta.

Figure 3A:
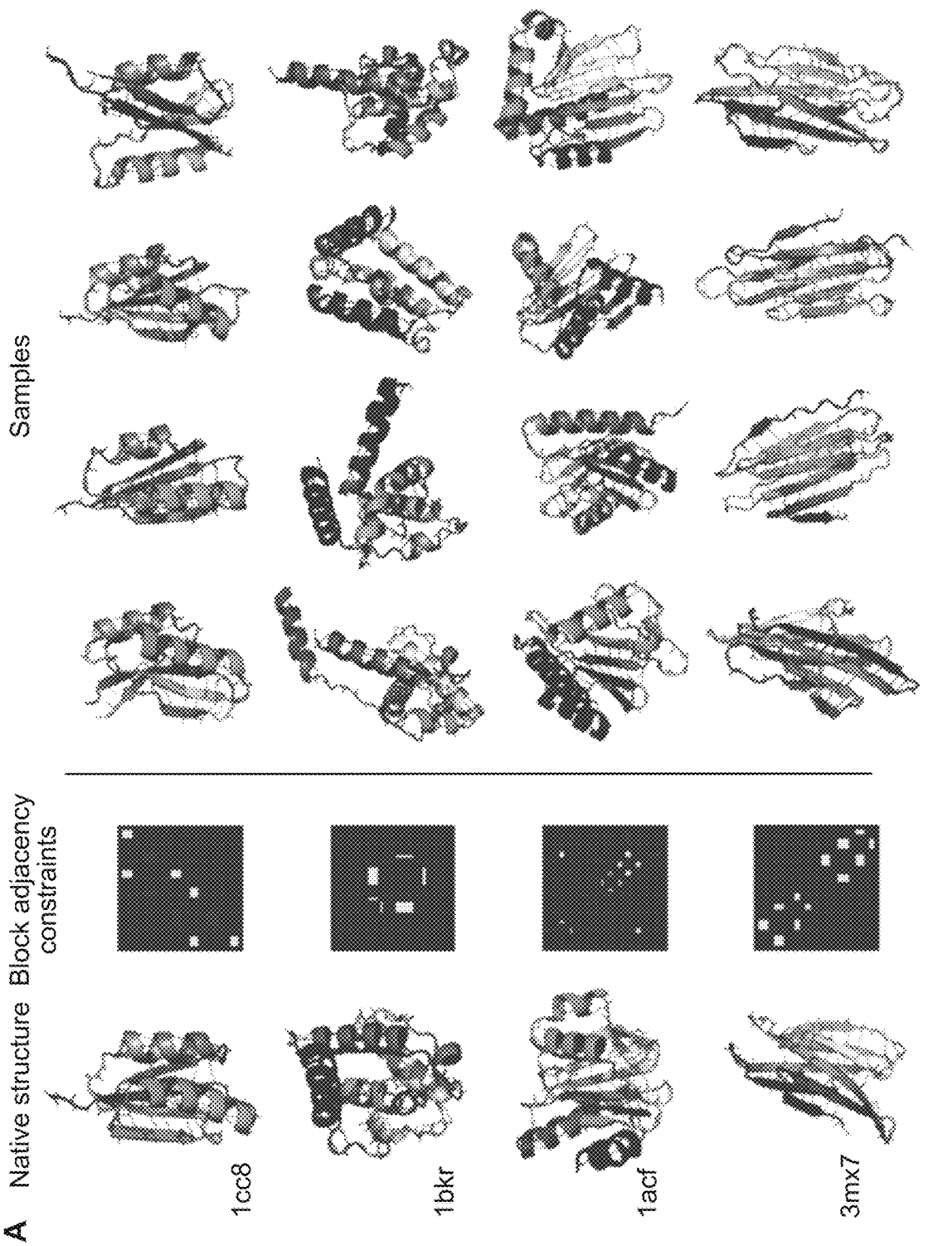
FIGS. 3A and 3B illustrate an embodiment of from—scratch protein generation.
Figure 3B:
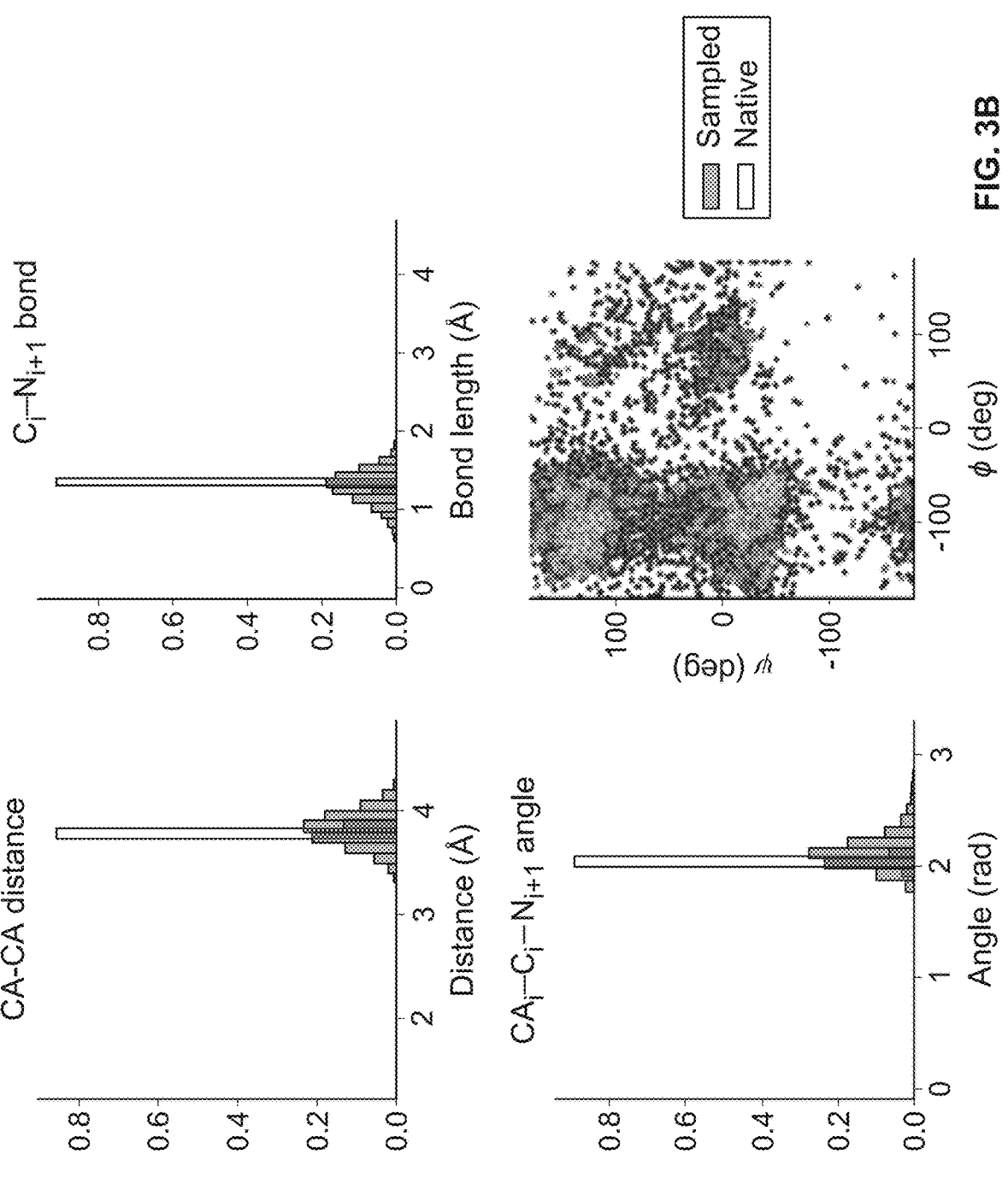

FIGS. 3A and 3B illustrate an embodiment of from—scratch protein generation. FIG. 3A shows four different sampling scenarios. As shown in this example, the block adjacencies are shown in the middle and a test set structure matching the adjacencies is shown on the left. On the right are shown four different samples from the model with no post-processing. As shown in this example, the samples show a high degree of variability and excellent hydrogen bond patterns (the dashed lines) within helices and between beta sheets.

As shown in the example of FIGS. 3A and 3B the model is able to produce structures that are highly variable and physically plausible. In the example of FIG. 3B, four samples are selected from the PDB and, for each one, the block adjacency and parallel/anti-parallel constraints are shown, as well as four high-fidelity samples from the model. As shown in this example, the samples are of high quality, with hydrogen bonds within the helices as well as between the beta sheets. In this example, the beta sheet bonds are especially challenging to synthesize because the local structure needs to be precisely correct for the bonds to form, which in turn imposes constraints on the global structure to support the positioning of the sheets.

Quantitatively, the charts shown in the example of FIG. 3B illustrate that the model has learned physical priors of proteins directly from the data distribution. The various bond lengths and angles show good histogram overlap between the native and sampled structures. The Ramachandran plot of torsion angles $\phi$, $\psi$ between adjacent $C_\alpha$ frames shows consistency between the native and sampled distributions.

Sequence Design and Rotamer Packing (Fixed Backbone Sequence Design)

As described above, the techniques described herein are used to perform various protein design tasks. For example, the generative models are used to generate backbone structures. A backbone by itself is not necessarily sufficient, as a sequence may be needed that will fold the protein into a structure that can be tested in the laboratory setting. In various embodiments, the sequence design task involves determining various strings of amino acids such that, when in the laboratory setting to actually express the protein, the amino acids will fold into the desired structure. In some embodiments, the generative models described herein are usable to design sequences onto such backbones. A protein is then generated based on the combination of the generated backbone and the sequences generated on those backbones.

With respect to sequence design, with a starting backbone, the models described herein are also usable to redesign a sequence, and generate a distribution of sequences that will fold to that backbone.

For example, given a fixed backbone structure (tertiary structure or protein domains with desired conformation with a desired arrangement of alpha helices, beta sheets, and other folds) as input, the model determines sequences of amino acids that will fold into the desired shape.

That is, starting from an existing backbone, the model designs-in side chains such that the amino acids (which are defined by the side chains, as well as the corresponding portion of the amino acid that contributes to the overall backbone), when in some sequence, will fold into the desired shape (or backbone structure/topology that the side chains are attached to).

Figure 4A:
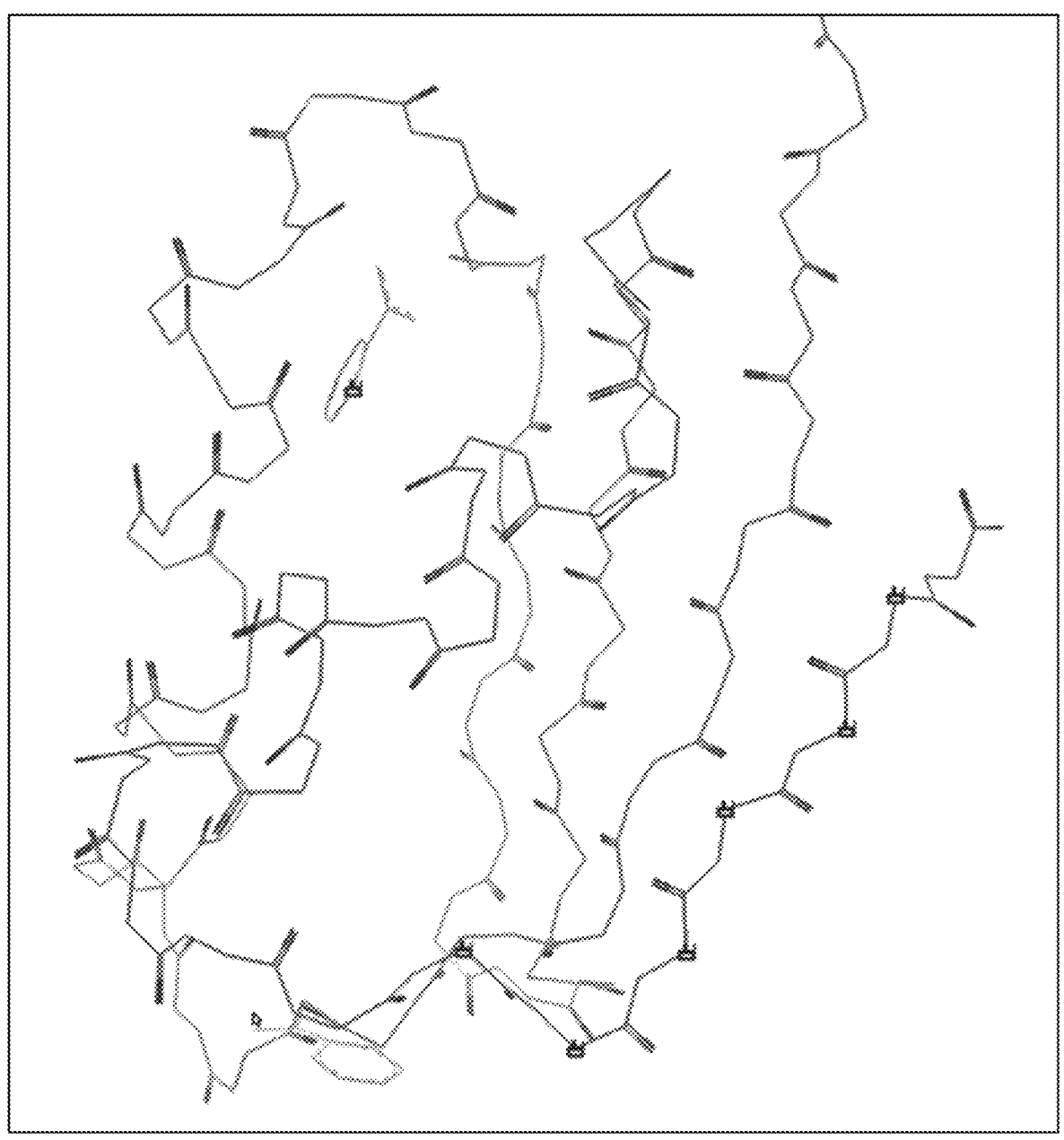
FIG. 4A illustrates an embodiment of backbone atoms of a protein backbone structure.
Figure 4B:
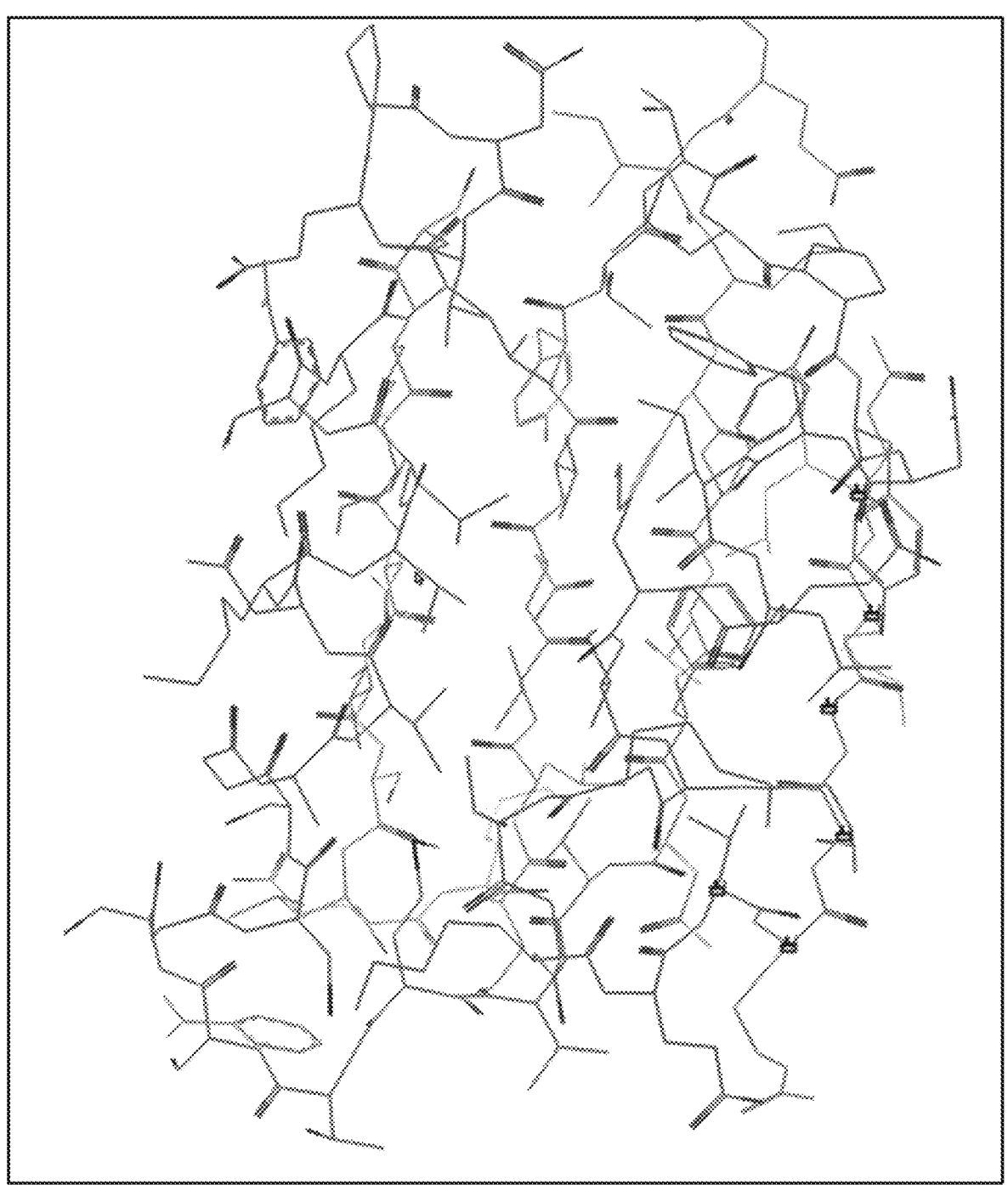
FIG. 4B illustrates an embodiment of a protein structure with side chains.

FIG. 4A illustrates an embodiment of backbone atoms of a protein backbone structure. FIG. 4B illustrates an embodiment of a protein structure with side chains. Using the sequence diffusion modeling described herein, a backbone topology as shown in the example of FIG. 4A is provided as input to the sequence diffusion model (e.g., where the representation of the protein structure is provided as an input constraint), and the sequence diffusion model is sampled to output a predicted amino acid sequence that will fold into the backbone topology (adhering to the topology constraints).

In the case of backbone generation, the backbone atoms are known, but not necessarily the side chain atoms. As described above, while there is the same repeating pattern on the backbone, the protein is uniquely identified based on its side chains, which also causes the protein to fold in a particular manner.

The following are further embodiments of fixed backbone sequence design with diffusion models. This includes determining, given a backbone, the sequence that will cause the chain to fold into the backbone shape. In some embodiments, the process begins with a backbone. A sequence is then designed on the backbone. That is the model takes as input a backbone and produces a sequence. For example, the side chain identifies or the amino acid string for the input backbone is predicted.

In some embodiments, when using the diffusion models described herein, a backbone and a noised sequence are provided as input to the diffusion model. The diffusion model provides as output a de-noised sequence.

For example, during training, the ground truth in the training data includes, for a protein, both a ground truth backbone structure representation, as well as a ground truth sequence. The backbone is fixed during training, while the ground truth sequence is diffused towards a noised sequence during the training. The diffusion model is trained to de-noise the noised sequence back to the ground truth sequence (which is what caused the backbone structure to fold into some shape). In this case, diffusion on a discrete object is performed, as each element of the sequence is one of 20 amino acids.

In some embodiments, fixed backbone sequence design includes rotamer repacking with diffusion. For example, the side chains that branch off of the backbones may branch off in various ways, and may adopt different rotamers. In some embodiments, diffusion models are used to pack the rotamers for a structure. In some embodiments, fixed backbone sequence design includes rotamer repacking with diffusion.

As described above, in addition to facilitating structure generation, embodiments of the generative diffusion models described herein are also usable to perform sequence design and rotamer packing. As one example, the model's ability to recover ground truth sequences and rotamer configurations on native structures is measured, because the physical variation in sampled structures implies a different set of optimal residues and rotamer configurations which cannot be compared to the ground truth directly. In this example, the sequence recovery rates are compared across 50 sampled sequences, each starting from the native full-atom backbone with no side-chain information.

Figure 5A:
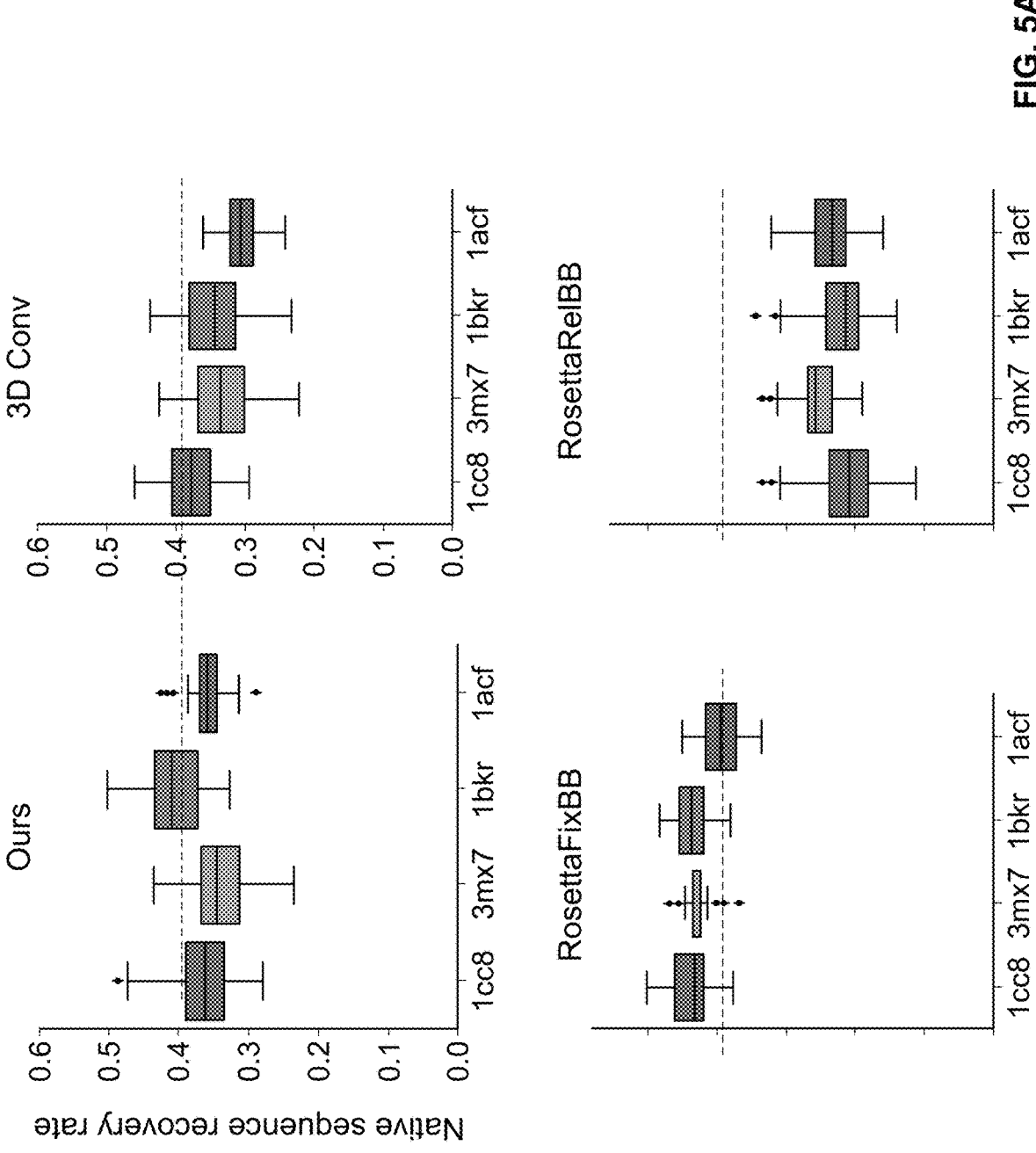
FIGS. 5A-5C illustrate embodiments of sequence design and rotamer repacking.
Figures 5B, 5C:
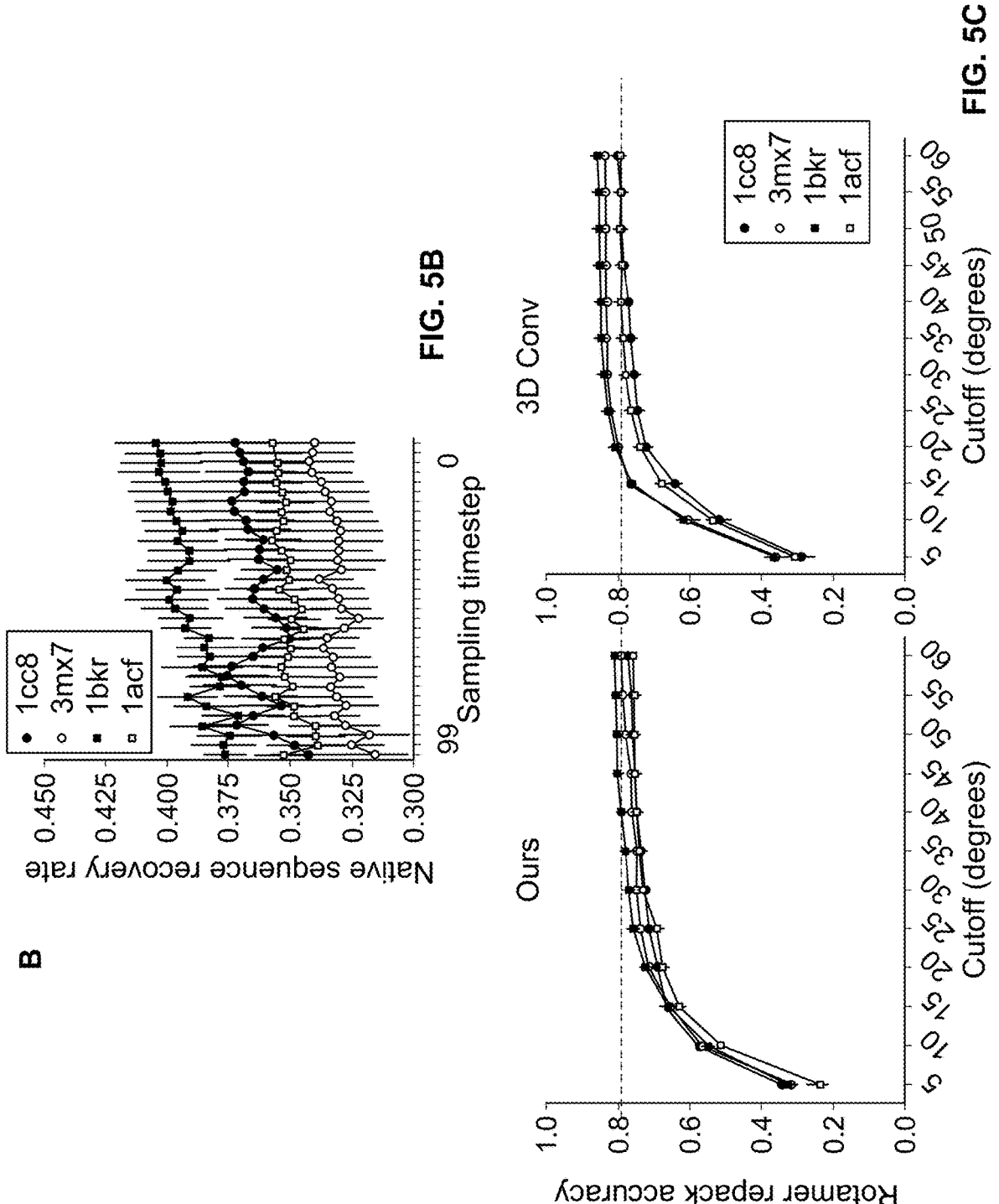

FIGS. 5A-5C illustrate embodiments of sequence design and rotamer repacking. The example of FIG. 5A reports native sequence recovery rates across 50 designs for test case structures. The example of FIG. 5B shows the sequence recovery rate during the sampling trajectory, starting from predicting from all masked tokens. The example of FIG. 5C shows the rotamer packing accuracy after $\chi$ diffusion as a function of degree cutoff. This approach to sequence design and rotamer packing is comparable to baselines and faster by an order of magnitude.

As shown in the example of FIGS. 5A-5C, the model has comparable sequence recovery performance to baselines. The 3DConv baseline refers to a machine learning approach using 3D convolutions. RosettaFixBB and RosettaRelBB are baselines using heuristic energy functions; RosettaFixBB holds the backbone fixed during sequence sampling, which, for example is a similar setting as an embodiment of the model described herein, and RosettaRelBB allows it to vary slightly in a "relaxation" procedure. The rotamer packing performance is comparable at the most stringent metric cutoffs (5 and 10 degrees).

Joint Backbone and Sequence Design

The generative model described herein may be variously adapted to accommodate jointly handling backbone generation and sequence design. The techniques described herein may be used to provide an output that is not only the backbone (where a sequence is then designed), but an output in which both the backbone and the sequence are provided together, simultaneously, in a corresponding manner. For example, there is a correspondence between the backbone and the sequence that are outputted so that the sequence will fold back into the backbone (as the combination of the backbone and the sequence represents the same molecule).

In some embodiments, this design task involves generating an entire object or protein domain, either unconditionally or given some conditioning constraints, in which both a desired 3D protein structure, and the sequence of amino acids (side chains) that would fold into that 3D structure are jointly generated.

The following are embodiments of jointly handling structure and sequence. In some embodiments, jointly handling structure and sequence includes generating not only the backbone, but the sequence as well. For example, the entire structure of the protein, including backbone and side chains is predicted.

Figures 6A, 6B, 6C:
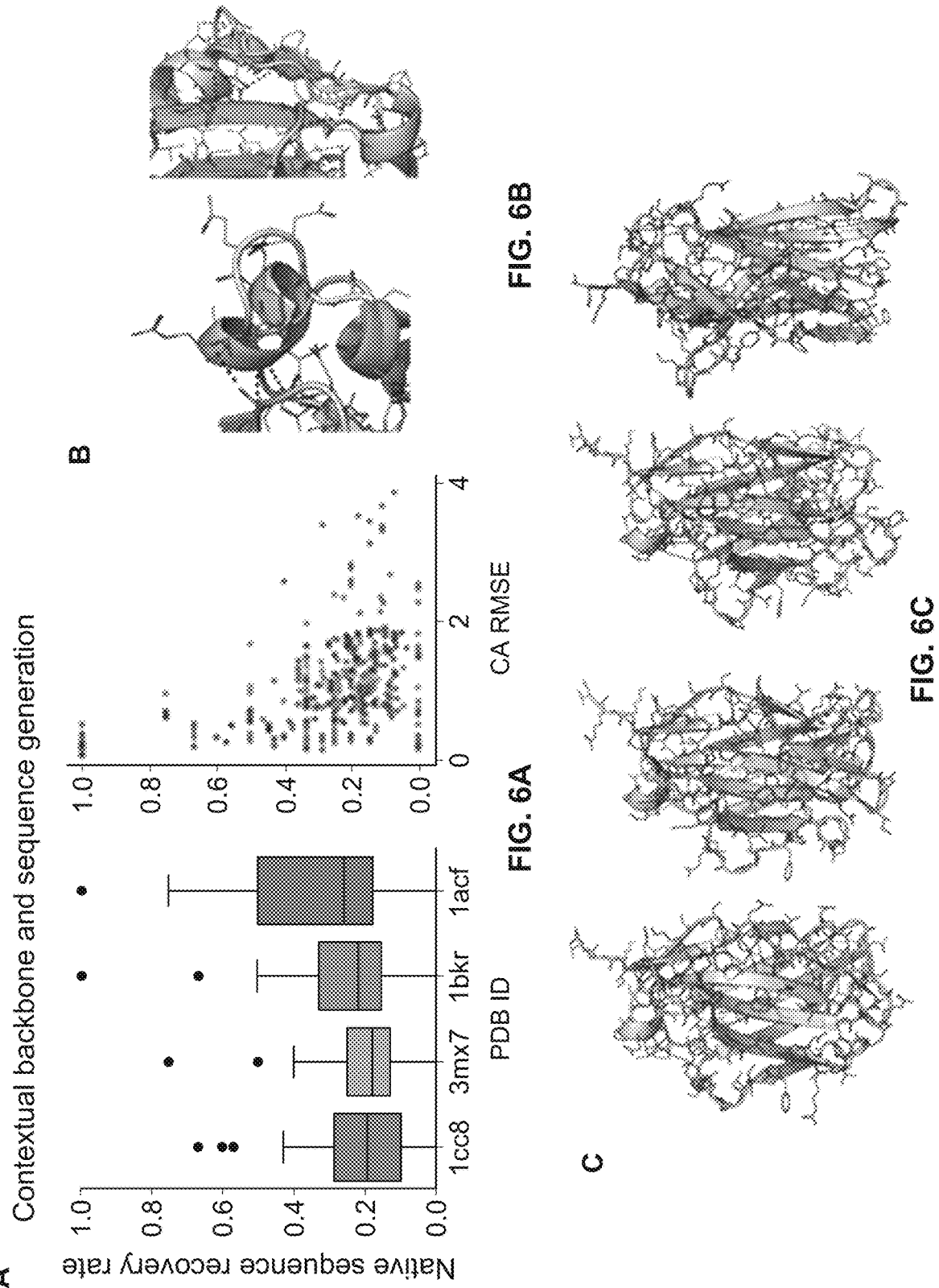
FIGS. 6A-6C illustrate embodiments of contextual joint sampling of sequence and structure.

FIGS. 6A-6C illustrate embodiments of contextual joint sampling of sequence and structure. For the cases shown in this example, rotamers are packed with the rotamer diffusion model. The example of FIG. 6A reports native sequence recovery rates and $C_\alpha$ RMSE (root mean square error) after inpainting masked regions of test case proteins and sampling both backbone and sequence. Shown in this example is that for some cases, the model can nearly recover the native loop and sequence. FIG. 6B illustrates examples of model generated loops and sequences with the native backbone for context. The example of FIG. 6C illustrates, given a fixed immunoglobin backbone and sequence, joint sampling of variable-length loops and residues.

In some embodiments, in the joint approach, a noised structure (backbone) and a noised sequence are both provided as input to the diffusion model, which then jointly de-noises the input noised structure and noised sequence. The output is a refined backbone structure (e.g., backbone, with localized secondary structures folded in some conformation) and a refined sequence (e.g., amino acid string and side chain elements, where the sequence is the amino acids, where each amino acid has a unique side chain group). In some embodiments, a rotamer refers to the conformation of a side chain (e.g., direction that the side chain is pointing out from backbone).

In some embodiments, the sequence de-noising is performed for a subset of the time. For example, de-noising of the sequence is started or initiated after a reasonable example of the structure is obtained. In some embodiments, conditioning on the noised sequence is performed. In some embodiments, conditioning is jointly performed.

In some embodiments, to facilitate joint structure and sequence prediction, a model is trained to jointly diffuse structure and sequence concurrently. As one example, structure variables $x_{C_\alpha}$ and q are diffused for the full $T_{structure}=1000$ steps with the diffusion training and sampling approaches described above. In some embodiments, the sequence variables r are diffused from $T_{sequence}=100$ to T=0, with an additional network that conditions on the output of the structure component of $\mu_\theta$ at each step. That is, for a given $0 \leq t \leq 100$, a masked prediction of the sequence is performed according to a schedule, conditioning on the prediction of $\hat{x}_{C_\alpha}^0$ and $\hat{q}^0$ from the structure network. In some embodiments, rotamer diffusion is then run on the sampled backbone and sequence.

In the example of FIG. 6A, contextual inpainting of both the backbone and sequence are performed. Further details regarding inpainting and controllable generation are described below. The model is found to be able to at times nearly recover the native solution both in terms of native sequence and backbone atom positions for inpainted regions. This type of a model facilitates, for example, full-atom loop generation (as shown in the example of FIG. 6B), where both the loop backbone and candidate sequence for the loop region are jointly generated. This capability provides an avenue to various engineering challenges, such as immunoglobin (Ig) loop design. Antibody variable Ig domains host highly variable CDR (complementarity-determining region) loops that allow them to selectively bind practically any target. FIG. 6C illustrates how this type of generative model can be used to vary the CDR backbone loops and sequence jointly on a fixed Ig backbone.

The trained joint diffusion model is then sampled jointly over backbone and sequence in a manner that is self-consistent—namely, that the generated sequence folds to the generated backbone structure.

Multi-Conformation Structure Prediction

Another example limitation of existing techniques for protein structure determination is that existing models, such as existing supervised learning frameworks, generate a single output or solution from a single input (e.g., constraints on the conditions for the output to be generated). That is, there is a limit on the number of outputs that are provided given an input constraint, which is restrictive for engineering tasks, where it is desirable to have many solutions to work from.

Embodiments of the generative model described herein allow for, given an input constraint or conditioning information, multiple solutions to be provided as output. This is an improvement over existing modeling techniques, which provide a more limited output. For example, using the improved generative modeling techniques described herein, a distribution of structures may be sampled, which is beneficial for engineering tasks. For example, this is beneficial in the context of drug or pharmaceutical design, where given a constraint on a target (e.g., the location of binding the target, various properties of interest for the drug, etc.), the improved generative models described herein facilitate the sampling of numerous possible candidate drugs.

As described above, the generative models described herein facilitate structure prediction. In some embodiments, the generative model is adapted to take as input a sequence and outputs a predicted structure. In reality, these proteins may adopt more than one structure, where there may be flexible in certain regions. That is, there is a distribution of states that a protein may adopt. In some embodiments, the generative models described herein are configured to perform multi-conformation structure prediction.

In some embodiments, the diffusion model is trained to predict structure from sequence. For example, the model takes as input a sequence and provides as output a distribution of backbone structures. For any given protein, there is a sequence and a structure. Historically, there is access to numerous protein sequence data from genome sequencing, but there is a sparsity of structure data. Thus, it is challenging to predict structure from sequence with existing techniques.

The diffusion and generative models described herein address such issues. For example, proteins are flexible objects that can adopt different conformations. For example, when two proteins bind, they will deform and change shape as part of the binding event.

In some embodiments, the diffusion models described herein are trained to take in as an input a sequence and predict not only a single structure, but a distribution of structures. For example, different secondary elements or regions of the protein may have various amounts of degrees of flexibility (e.g., allowing regions to dislodge and interact).

In some embodiments, the diffusion models are trained for multi-conformation structure prediction, where the diffusion model is trained to start from a sequence and predict and model which regions are more conformationally flexible. Rather than providing a single snapshot as output, a distribution of structures is provided as output. In some embodiments, the distribution of structures is overlaid with the predictions. For example, the model provides a prediction of flexibility of different regions of the structure, the stability of various regions, whether some region is dislodged, etc.

In this example, the model architecture described herein is adapted to take as input sequence information, where the diffusion model is requested to predict the backbone structure. In some embodiments, the diffusion model is configured to sample multiple possible states of the structure. This is an improvement over existing systems that provide a single output for a single input (that is, existing techniques do not provide multiple possible conformations for a single sequence).

As one example of performing multi-conformation structure prediction, when using embodiments of the diffusion models described herein, the sequence is specified as the constraint, and the diffusion model is tasked with performing structure prediction. This provides the ability to sample multiple conformations of the protein. The multiple conformations or variations of the backbone structure are determined as variants by repeatedly running the diffusion model with the same sequence as a constraint, but with different randomly sampled noise as input (for the diffusion model to denoise). The model may be run with as many randomly sampled noised inputs as desired to generate various potential conformations of the sequence constraint.

Embodiments of the multi-conformation structure prediction described herein use diffusion to predict multiple conformations of a backbone structure (as opposed to a single predicted structure).

In some embodiments, by being able to generate multiple conformations for the same sequence, uncertainty is quantified via measurement of the spread of predicted backbone structures. This includes assessing conformational flexibility.

Inpainting and Controllable Generation

In some embodiments, the model described herein is also suitable for the task of completing existing proteins. In some embodiments, the diffusion models described herein are adapted to perform inpainting. In some embodiments, when performing inpainting, a portion of the structure is provided as part of a constraint.

As one example, to facilitate this task, an additional model $\mu_\theta$ is trained to condition on existing structures by holding parts of the structure fixed during training and executing the forward diffusion process on the complement of the fixed parts. In some embodiments, for each datapoint during training, "block diffusion" is executed with, for example, probability 0.6 (or any other probability as appropriate) and "contiguous diffusion" with, for example, probability 0.4 (or any other probability as appropriate). In some embodiments, in block diffusion each loop diffuses towards the prior with, for example, probability 0.25 (or any other probability as appropriate), and the other blocks with, for example, probability 0.025 (or any other probability as appropriate). In some embodiments, in contiguous diffusion, contiguous blocks are chosen at random to diffuse towards the prior with, for example, probability 0.03 (or any other probability as appropriate) for each starting residue and with length distributed uniformly between, for example, 1 and 15 (or any other values as appropriate). In some embodiments, for all residues that do not diffuse toward the prior, their position is held fixed at their ground truth positions during training and during sampling.

Figure 7A:
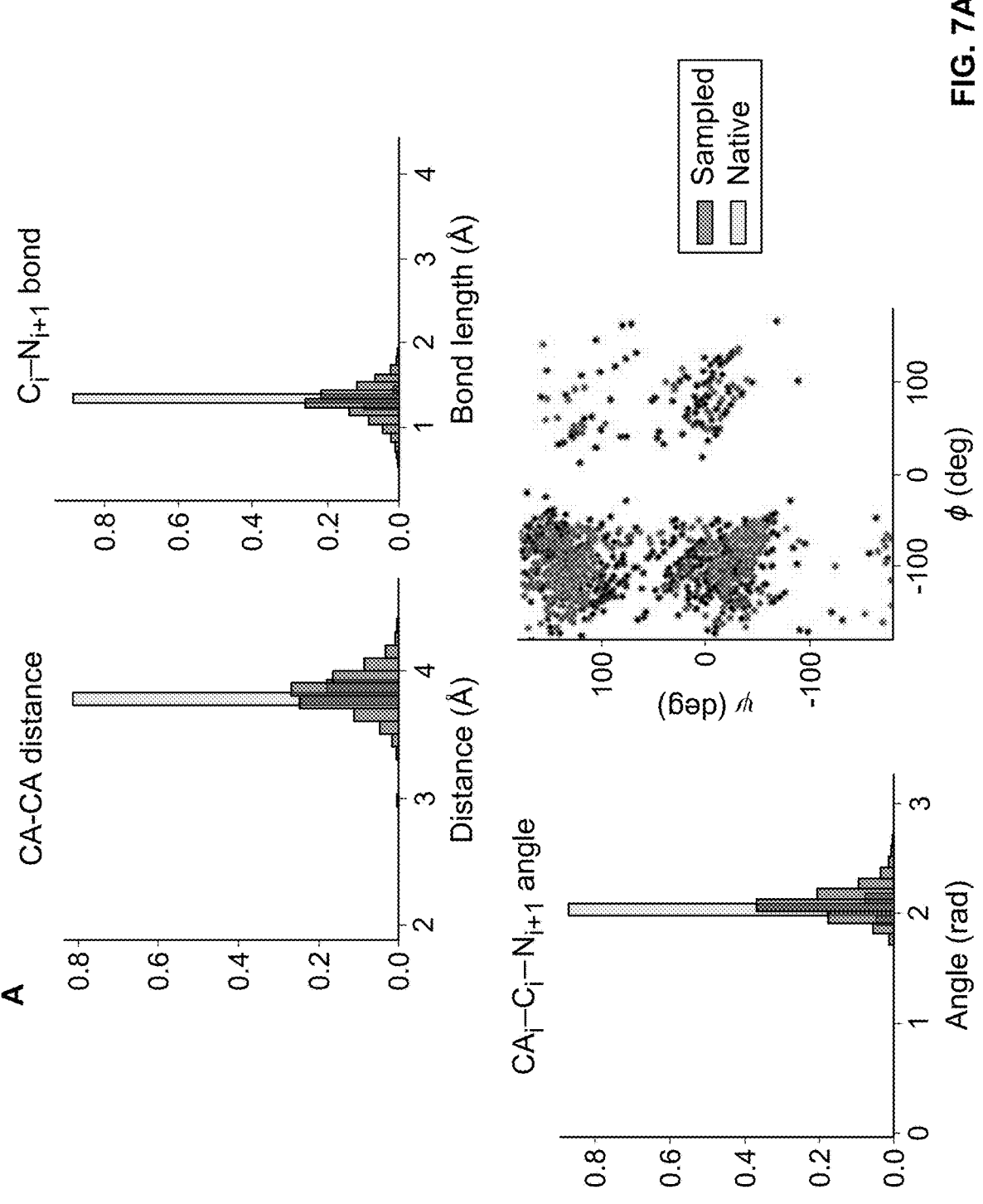
FIGS. 7A and 7B illustrate an embodiment of loop design.
Figure 7B:
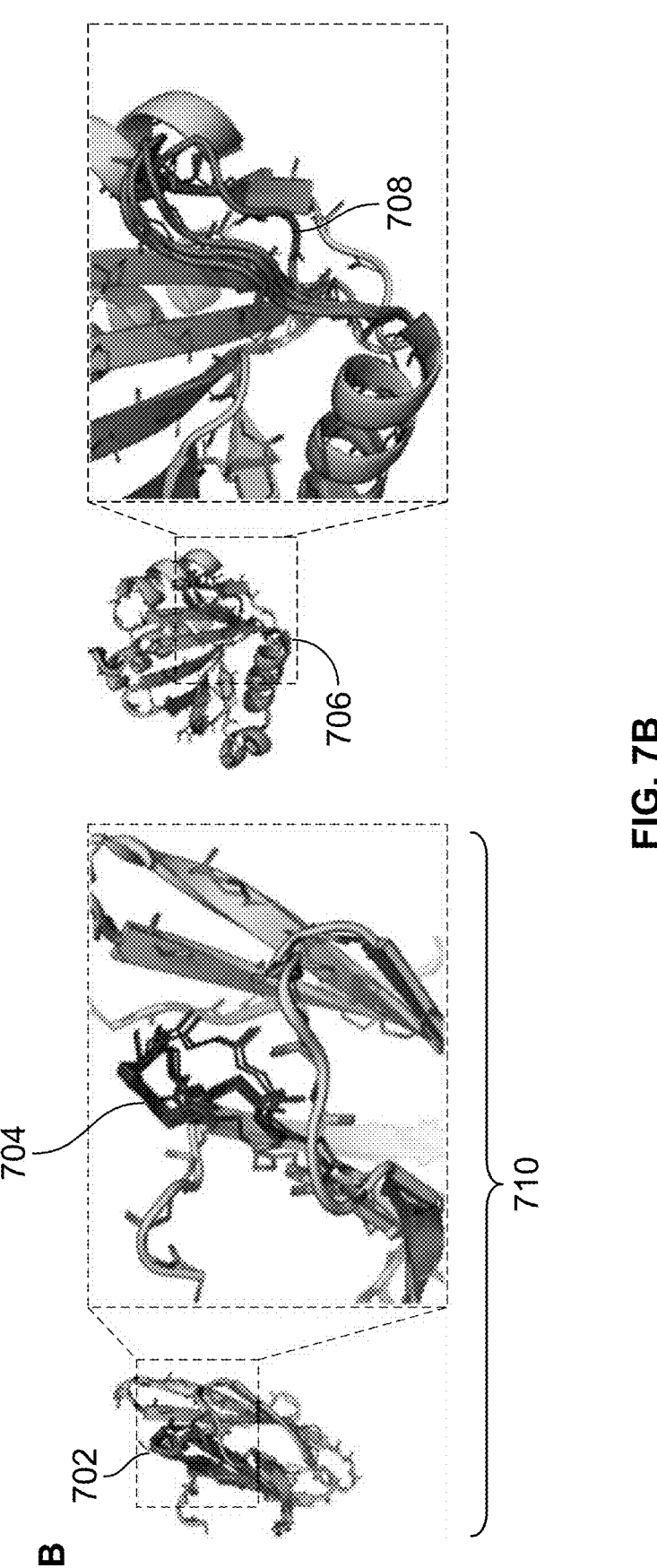

FIGS. 7A and 7B illustrate an embodiment of loop design. In this example, the loop completions of the model are highlighted at 702 (and expanded at 704) and 706 (and expanded at 708. In this example, FIG. 7A compares the distributions of bond lengths and angles for the completed regions. The example of FIG. 7B shows examples of loop completions. The image on the left 710 highlights the model's ability to find discrete modes of the possible loop configurations.

FIGS. 7A and 7B also illustrate that the distribution of bond geometries for the in-painted regions is consistent with the corresponding distribution in the native structure. As also seen from the samples, the model finds discrete modes of the loop distribution at the atomic level.

In some embodiments, the model can go beyond sampling variants of sections of existing proteins, to modifying the sections themselves. In this case, the same underlying $\mu_\theta$ model as for the in-painting case is used, but in some embodiments at sampling time, the secondary structure and block adjacency conditioning information is modified.

Figure 8:
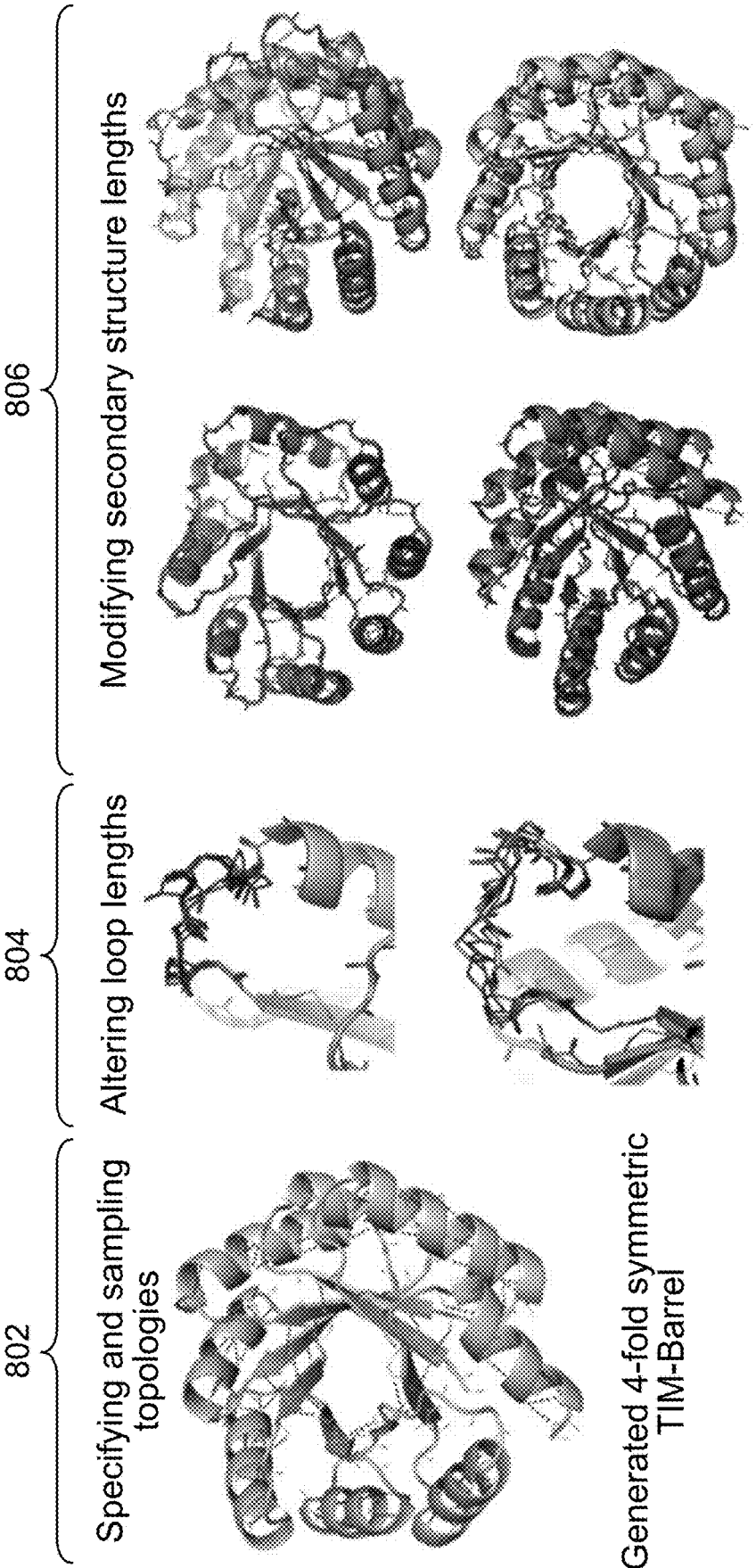
FIG. 8 illustrates an embodiment of controllable generation.

FIG. 8 illustrates an embodiment of controllable generation. In various embodiments, the model facilitates many modes of controllable generation of protein structure and sequence. Here, in the example of FIG. 8, are shown (at 802) new and/or idealized topology generation, (at 804) loop engineering, and (at 806) secondary structure modification. Extensions to this include using sampler guidance to enforce specific constraints such as distance between elements, designing sequences onto generated structures or structural elements, and jointly sampling sequence and structure.

As shown in the example of FIG. 8, the model is able to extend loops and replace beta sheets with helices in physically plausible ways. These synthetic structures are distinct from the natural structures found in the PDB, which indicates that the model has encoded useful physical priors for use in sampling.

Embodiments of Providing Constraints During Sampling of Diffusion Model

The following are embodiments of providing constraints on which to condition the model (analogous, for example, to entering a prompt in ChatGPT or DALL-E). In some embodiments, the constraints or conditions are specified in a manner to support controllably generating proteins of arbitrary shapes or various other tasks, as described above. Embodiments of programmatic, controllable techniques for conditioning are described below. For example, using embodiments of the conditioning techniques described herein, users are able to, in a programmatic, controllable way, change the length of barrels, change the length of helices, etc.

As described above, one example compact representation includes describing a (desired) protein in terms of its secondary structures, as well as adjacency information. For example, conditioning is done on the secondary structure, such as specifying:

Desired Secondary Structure Elements: Such as helices, loops, beta sheets, etc. This includes providing conditions on the appearance or elements of the structure to be generated. As one example, a user may specify, via their prompt, that they would like a helix, then a loop, then a beta sheet, then another loop, and then a helix. In some embodiments, the conditioning information includes the number of secondary structure elements, their sequence, as well as the dimensions of the elements (e.g., length)

Adjacency Information: In some embodiments, the conditioning information includes coarse adjacency information. The adjacency information includes positional and orientation information for (at least some of) the specified secondary structure elements, and define, for example, the shape or topology of the backbone structure made up of the selected secondary structure elements. For example, the user may specify that they would like two helices to be next to each other. Specification of adjacency information may be at various granularities. As another example, users may provide as input conditions such as prompts indicating what secondary structures are to be paired together (e.g., pair two particular strands together), what secondary structure should be separated (e.g., separate these two particular strands), position of secondary structure within the overall shape (e.g., move this helix over to the side). That is, the adjacency information includes specifying input conditions that allow control over the shape or topology of the molecules.

In some embodiments, to facilitate such types of conditioning information, each and every contiguous region of secondary structure is represented as a block. For example, each different secondary structure element is represented with a corresponding block representation, such as alpha helix blocks, beta strand blocks, and loop blocks. The conditioning information is structured to allow users to specify information about the adjacency and proximity of these different elements relative to each other. For example, users are able to specify one beta strand to be parallel to another beta strand, which should then be antiparallel to another beta strand. The user can then specify a helix to be sitting adjacent to the beta strands. The user may then specify that they would like another helix to be next to that helix, or instead to be behind the beta sheet. That is, the user is allowed to specify block adjacency with a coarse specification, which is then sent in as an input to the model.

In addition to coarse targets, fine-grain conditioning is also supported, where, for example, specification of exact pairwise distances between secondary structure elements is supported.

The platform supports various formats of conditioning information. As one example, the user conditioning input is received via text prompts. As another example, the conditioning information is provided via a graphical user interface (GUI). For example, the user can drag representations of secondary structure elements and position or orient them as desired. As one example, the interfaces are provided in part by front end interface 122, with display of constraints and receipt of user constraints handled in part by constraint engine 128.

Figure 9:
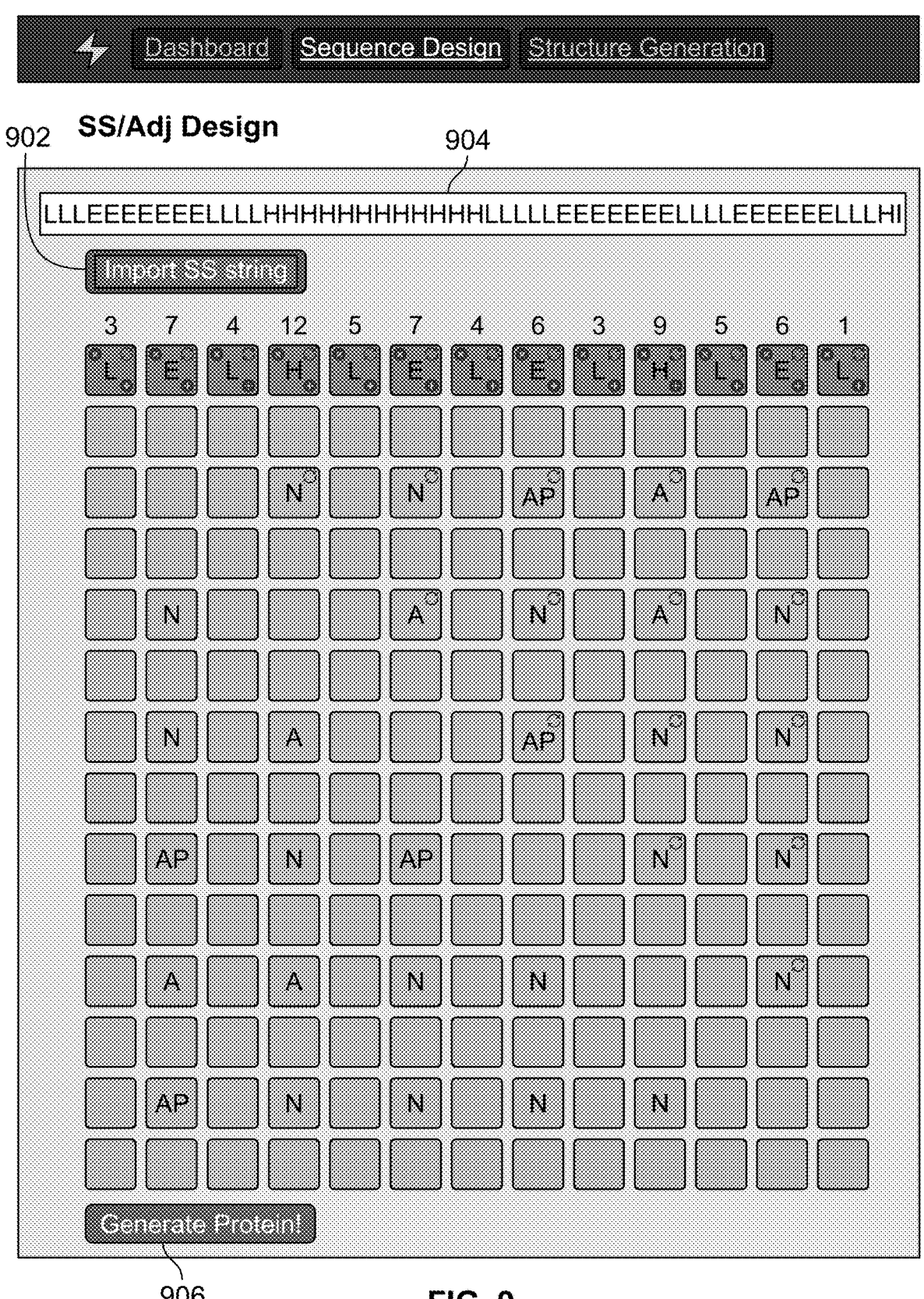
FIG. 9 illustrates an embodiment of user specification of conditioning information.

FIG. 9 illustrates an embodiment of user specification of conditioning information. As shown in this example, the user is provided user interface elements by which to change secondary structure string and change block adjacencies. For example, via the user interface, the user specifies the secondary structure elements of a sequence, as well as the adjacency of the various elements.

For example, the user interface includes a dashboard with different pages for different types of tasks, such as sequence design and structure generation. As one example, under the structure generation tab, the user is provided the option to enter a secondary structure string.

In other embodiments, the graphical user interface allows a user to click and drag and move secondary structures around the interface.

Via the graphical user interface, the user is able to change the size of secondary structures (e.g., extend a helix in the string), add a block to the string, etc. The platform also provides the capability to change the secondary structure string itself. For example, the platform provides the option to change the type of block/secondary structure element from one type to another (e.g., from a loop to a helix to a beta strand). The platform also provides the ability for users to manipulate adjacency information, such as changing adjacency status from adjacent to non-adjacent (or vice versa), or from parallel to anti-parallel (or vice versa) for beta strands, etc.

In this example, the user interface provides the user tools to modify an existing structure. As one example, the platform imports (e.g., via "import SS string" user interface element 902) the constraints of an existing structure. The user interface is configured to provide options to modify the existing structure, such as extending the lengths of different elements, changing components, etc.

In this example, text box 904 is an input element via which the user specifies a secondary structure string. The user is able to change the string in the text box. In this example, the user is able to type or otherwise input any combination of secondary structure elements (with L for loops, H for helices, and E for beta strands in this example). In this example, the length of a secondary structure element is determined by the number of repeating letters (e.g., a beta strand with two L's "LL" is longer than a beta strand with a single "L").

In other embodiments, the platform provides, via the graphical user interface, tools to create structures from the beginning.

In some embodiments, after the conditioning information has been specified, the user can start a protein generation job (e.g., by clicking on user interface element 904). This causes a protein generation job to be scheduled with a backend worker. The worker then executes the protein generation job according to the provided user conditioning input (e.g., by running sampling engine 106.

That is, for protein generation, the platform provides for various types of conditioning input, such as a specification of desired secondary structure elements (helices, loops, beta strands), their type and number and size, as well as adjacency information, which defines how the secondary structure elements are positioned relative to each other, with examples of positional or adjacency information including relative distance, parallel, antiparallel, orientation, or any other type of relative positional information as appropriate.

Other types of conditioning information may also be embedded and provided as input. Further examples of conditioning information include a target protein to which a generated protein is desired to bind to. As another example, to perform an inpainting task, a small portion may be excised. In inpainting, in addition to conditioning on various constraints, conditioning on the context around the structure is also performed. With respect to excising, this includes starting with a structure, and removing a portion of the structure. Another portion of the structure is sampled in order to complete the protein. In some embodiments, within inpainting, conditioning on the context of an existing structure is performed, where a gap in the structure is filled in with an element or elements that are contextually accurate and that respect the context. Further details regarding inpainting and controllable generation are described above.

Other types of conditioning information are also supported by the generative diffusion models described herein.

As one example, suppose that a generative diffusion model is built to design a therapeutic. As one example, the platform supports conditioning on a target protein. For example, suppose that protein to bind to the coronavirus spike protein is to be generated. The spike protein is provided to the model. During training, the model is trained to learn how to generate the binder.

As another example, the platform supports conditioning on an excised piece of a structure in order to guide (or otherwise provide a constraint) on the generative model to generate a protein that is relevant to the excised structure provided as an input condition.

As another example, the platform supports conditioning on an active site of an enzyme and generating a scaffold for the active site provided as conditioning input.

The above example conditioning inputs (e.g., block adjacencies, pairwise distances, structure fragments to scaffold on, targets to bind to, etc.) are but some examples of conditioning inputs that may be used to provide constraints on generated structures, and other types of conditioning information may be specified.

Training of conditional models such as those described herein is beneficial, as it allows users to specify the characteristics of the proteins they would like, where the trained conditional diffusion model then generates output protein structure samples that conform or adhere to the desired input characteristics. While embodiments of conditioning information are described herein, the generative model described herein may also be used to perform unconditional generation. For example, constraints or conditioning information need not be provided as input to the generative model, where embodiments of the generative models described herein generate structure from noise. For example, unconditional samples are generated by not providing conditioning information as input.

Further Embodiments of Protein Representation

As described above, in one embodiment, with respect to the backbone structure, for each residue, rather than representing all of the atoms in the residue that contribute to the backbone, the backbone portion of the residue is represented by alpha carbon backbone atoms for the residues, where each alpha carbon backbone atom is associated with its corresponding coordinate in 3D space and a corresponding canonical coordinate frame for the residue. The following are alternative embodiments of approaches for representing proteins.

Graph Pairwise Distance Representation

In an alternative embodiment, the structure is represented as a graph, where rather than considering coordinates in 3D space, the distance between every pair of atoms is determined. The distances between pairs of atoms, in aggregate, forms a structure. In this example, the generative model is a generative model on pairwise distances, similar to a generative model of graphs. One issue with the graph representation is with reflection about the origin. That is, a mirror reflection of a structure may result if only considering pairwise distances, where if the structure is flipped about the origin, the pairwise distances will not change, but the actual orientation will have changed. This reflection is an issue, as proteins are chiral and have a handedness, and the reflected structure may be nonphysical—that is, not physically realizable in the real world. The representation of protein structures as coordinates (e.g., in 3D space) and coordinate frames/quaternions avoids such issues.

While embodiments of the graph approach described herein may be used to build a network that is invariant to rotations and translations, the graph approach may also include reflections when decoding structure from the graph. In some embodiments, the use of IPA in the manner described above addresses reflections.

Representation of Proteins as Chains

In some embodiments, such as those described above, proteins are represented in part as coordinates. The diffusion process then involves diffusing on these coordinates. In the intermediate steps of such a diffusion process, the atoms of the protein are disjoint atoms in space.

In an alternative embodiment, the proteins are represented as connected polymers, where the protein is treated as a chain of atoms that remains connected through the diffusion/ noising process.

One issue with treating the protein as a chain is cumulative effects of errors. For example, suppose that the protein is modeled as a chain (analogous to, for example, a robotic arm that can be considered as elements and joints on a chain). A small error in one of the positions (of the atoms) will negatively affect every downstream position as well. That is, errors will accumulate if, for example, the protein is modeled using torsion angles of the backbone. The treatment of proteins, in part, as coordinates of atoms, as described herein, avoids issues with accumulation of errors in polymer representations of proteins.

Embodiments of Quality Control

In the example of platform 102 of FIG. 1, the protein prediction architecture includes quality control module 130. In some embodiments, the quality control module is configured to assess the quality of predicted outputs (e.g., generated structures, sequences, rotamers, etc.). For example, as described above, numerous samples of random noise can be taken and provided as inputs in combination with a same set of constraints, resulting in numerous variants of predicted structures being output that conform to the set of constraints. In some embodiments, the quality control processing is configured to assess the variants, and filter out high quality samples from lower quality samples.

In some embodiments, performing the quality checks includes checking whether the predicted structure adheres to the constraints (the predicted structures may be impacted by the level of specificity of the provided constraints).

In some embodiments, the quality control module includes evaluation pipelines. Examples of characteristics of the predicted output that are evaluated include, without limitation:

Local structure correctness

Global structure correctness

Bond lengths

Bond angles

Torsion of the backbone

If both the structure and sequence are predicted, if the structure that corresponds to the sequence is re-predicted, the amount of correspondence between the predicted structure and the generated structure (from the re-prediction).

Energy functions to assess hydrogen bonding, Van der Waals forces, etc.

Various different types of evaluation criteria may also be specified based on the type of structure being predicted. As one example, structures that are designed to be binders are subject to an evaluation pipeline with criteria pertaining to binders, such as the delta energy that corresponds to the binder/target interacting (as opposed to the binder and target existing independently), the ability to predict the binder and target in complex after being generated, etc.

Figure 10:
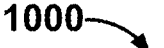
FIG. 10 is a flow diagram illustrating an embodiment of a process for training a protein diffusion model.
Figure 10:
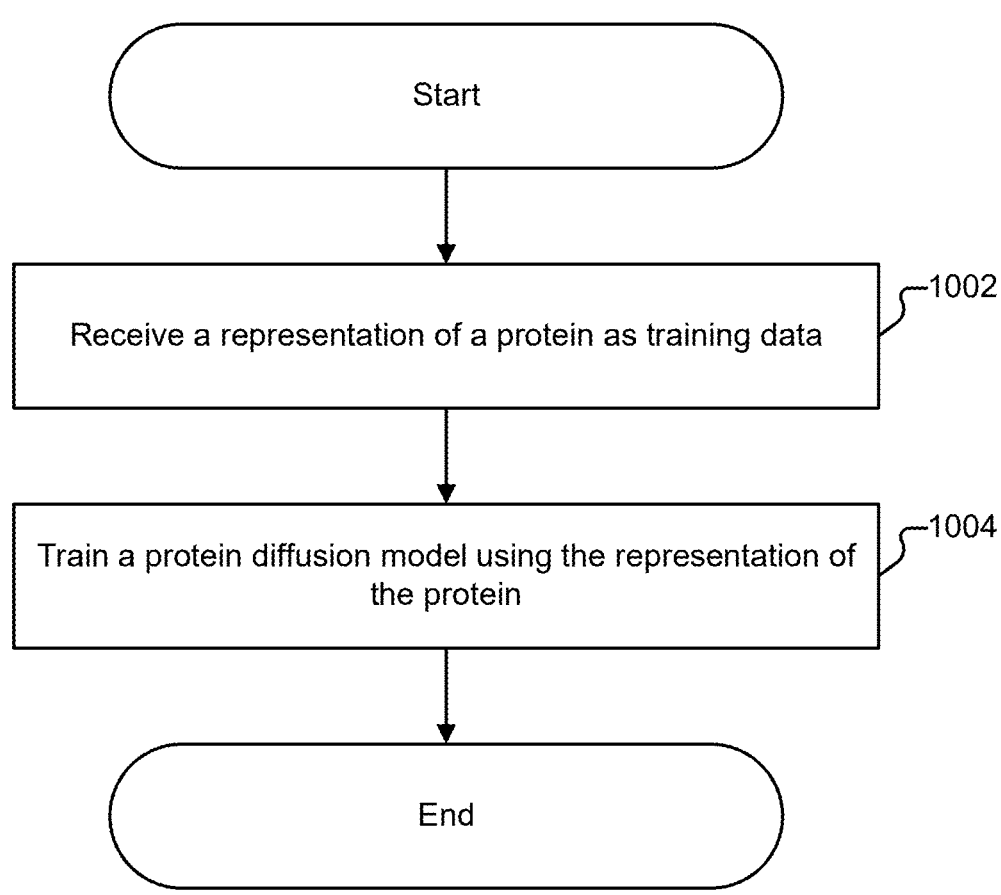

FIG. 10 is a flow diagram illustrating an embodiment of a process for training a protein diffusion model. In some embodiments, process 1000 is executed by training engine 104 of platform 102 of FIG. 1. The process begins at 1002, when a representation of a protein is received as training data. In some embodiments, the representation includes at least three dimensions. In some embodiments, the representation of the protein includes a backbone structure representation of a backbone of the protein. In some embodiments, the backbone structure representation includes, for an atom in the backbone, a corresponding coordinate and a corresponding local coordinate frame. As one example, the corresponding coordinate is a coordinate in three-dimensional space. In some embodiments, the coordinates in the representation correspond to positions of alpha carbon atoms in the backbone. In some embodiments, quaternions for the residues that include the alpha carbon backbone atoms are included in the representation.

In some embodiments, the representation of the protein includes a representation of a sequence of the protein (e.g., amino acids). In some embodiments, the representation of the protein includes a representation of rotamers of the protein (e.g., chi angles).

At 1004, a protein diffusion model is trained using the representation of the protein. In various embodiments, training the protein diffusion model includes performing structure diffusion, sequence diffusion, and/or rotamer diffusion, as described above.

In some embodiments, training the protein diffusion model includes performing rotational diffusion. In some embodiments, performing rotational diffusion includes diffusing rotations, such as rotating between rotational frames of reference (e.g., the local coordinate frames described above), as well as diffusing rotation (e.g., chi) angles of rotamers. In some embodiments, performing rotational diffusion includes performing interpolation. One example of interpolation is spherical linear interpolation. Further details and embodiments regarding diffusion of rotations are described above.

In some embodiments, training of the protein diffusion model includes determining parameters or weights of the protein diffusion model. In some embodiments, determining the parameters of the protein diffusion model includes computing a loss. In some embodiments, computing the loss includes performing alignment between rotational frames of reference. In some embodiments, the loss is computed according to a rotationally invariant loss function. Further embodiments and details regarding rotation invariance and loss functions are described above.

The following are further embodiments of diffusion processes, including structure diffusion processes for both 3D coordinates in 3D space, as well as processes for diffusing local coordinate frames.

In some embodiments, in 3D space, a scaled Gaussian is used, where the scale is changed based on the desired radius of gyration of the underlying domain. With respect to coordinate frames, in some embodiments, a random frame is sampled uniformly at random, such as SU(2) or SO(3) depending on whether considering quaternions or rotations. For example, a random rotation is sampled. In some embodiments, interpolation (where interpolation is an example mechanism to implement diffusion), such as SLERP (spherical linear interpolation), is used to smoothly interpolate between a ground truth coordinate frame at a given coordinate, and a randomly sampled coordinate frame.

The following are further embodiments of a protein diffusion model network for protein design. In some embodiments, the network includes self-attention, such as via a transformer-type architecture. In some embodiments, the network utilizes invariant point attention. In some embodiments, utilizing attention includes generating a model that is capable of performing lookups for regions that are spatially distant from each other.

Figure 11:
FIG. 11 is a flow diagram illustrating an embodiment of a process for sampling a protein diffusion model.
Figure 11:
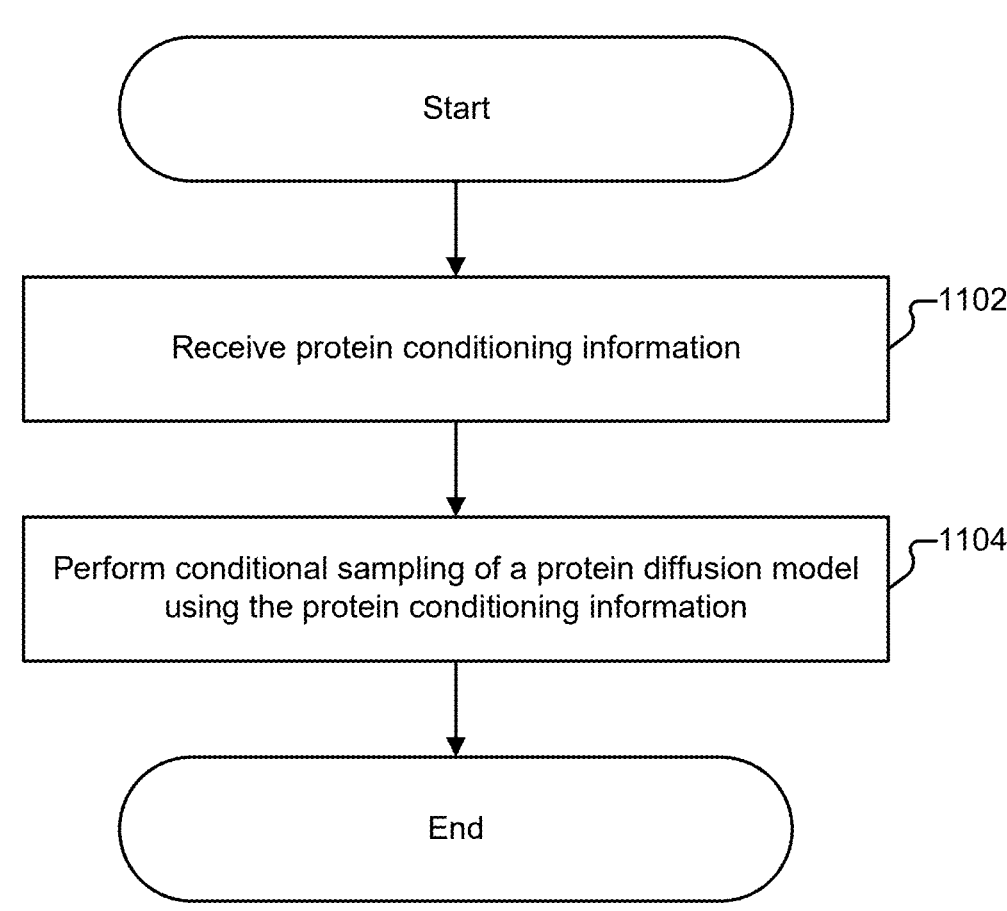

FIG. 11 is a flow diagram illustrating an embodiment of a process for sampling a protein diffusion model. In some embodiments, process 1100 is executed by sampling engine 106 of platform 102 of FIG. 1. In some embodiments, the process begins at 1102, when protein conditioning information is received. Examples of protein conditioning information (e.g., constraints) include structure constraints. In some embodiments, the structure constraints include constraints pertaining to secondary structure elements to include in a backbone structure, the relative positioning of one or more secondary structure elements, etc. Other types of information may be provided as constraints based on the type of prediction to be made. For example, as described above, in multi-conformation structure prediction, a sequence may be provided as a constraint across multiple instances of sampling of a protein diffusion model. Further examples and details regarding conditioning inputs are described above.

At 1104, conditional sampling of a protein diffusion model is performed using the protein conditioning information. In some embodiments, the protein diffusion model is trained using process 1000 of FIG. 10. In some embodiments, the protein diffusion model generates a protein structure or sequence in accordance with the protein conditioning information.

In some embodiments, quality checks such as those described above are performed on the protein prediction.

The following are further embodiments regarding sampling of a protein diffusion model. In some embodiments, to sample the generative model, noise (e.g., noised protein structure) and constraints are provided as input to the model, where the generative model then provides as output a predicted structure.

In some embodiments, the user provides a specification of desired constraints, without requiring the user to provide the noise. For example, the sampling engine 106 samples random noise and provides the constraints and sampled random noise to the generative model. The generative model then conditions on the constraints and makes predictions.

In some embodiments, the random noise is automatically sampled from a defined prior distribution. The generative model then outputs predicted structures, which, for example, include 3D point clouds (e.g., for alpha carbon coordinates). In some embodiments, at the beginning of the prediction process, there is little signal in the noise cloud. The model then interpolates that noise cloud toward a prediction. At the next time step, the output is effectively similar to noise, with somewhat more signal of an underlying structure. Now suppose that the model prediction is at a next time step. A new prediction is made. Again, there may or may not be some signal. The noise cloud is interpolated toward the prediction. By later stages, more signal (structure) emerges, and the noise is interpolated toward another prediction, such that there is more signal about the prediction containing underlying protein. The refinement process then continues. Other types of protein-related outputs may be generated as well, such as sequence, inpainting, etc. Further details regarding design tasks supported by protein diffusion models are described above.

One advantage of the generative techniques described herein, as compared to existing supervised learning techniques, is that numerous samples can be drawn, with variance in those samples. This results in numerous solutions being able to be generated (although constraints may be provided that could cause the outputs to be self-similar).

In some embodiments, a random noise cloud is sampled. The sampled random noise cloud, as well as constraints, are provided as input to the model. Diffusion is performed (de-noising), and one structure is provided as output. For example, one combination of a random noise cloud and a set of constraints yields one predicted (refined) output structure. Many noise clouds may be randomly sampled and provided to the model with the same constraints, resulting in multiple variations of output structures that conform to the constraints. If, however, the problem being designed for is highly constrained, then this may result in results becoming self-similar.

As described above, various design tasks such as arbitrary backbone design (e.g., of protein domains), fixed sequence design (e.g., given a backbone, design a sequence), and joint structure-and-sequence design (e.g., performing both backbone and sequence design jointly, where not only the backbone of the protein produced, but also the sequence that would fold onto that backbone structure/shape) are facilitated using the improved classes of generative models described herein. In some embodiments, the joint structure and sequence design process includes determining, given a set of constraints, how to sample an entire distribution of backbone structures, sequences (given a particular backbone structure), or both the backbone structure and sequence in tandem, that adheres to the set of design constraints. That is, embodiments of the design process using protein diffusion models described herein are used to generate structure and sequence, where in addition to generating arbitrary length protein domains (e.g., backbones) of extremely high quality conditioned on design constraints, embodiments of the design techniques described herein are also usable to perform fixed backbone sequence design, as well as joint structure and sequence generation.

As described above, one example task accomplished using embodiments of the generative model described herein is to create protein backbones. Another example task supported by the generative techniques described herein is sequence design. This includes designing of sequences of amino acid side chains that branch off of protein backbones.

For example, the sequences of amino acid side chains that branch off of the backbone impact the three-dimensional folding of the proteins.

The generative techniques described herein support generating of backbone structures, which include helical and sheet-like elements, such as beta strands, where such structures, for example, form paired strands of parallel or anti-parallel beta strands that then fold into a helical structure. The generative models described herein are sufficiently powerful to perform low level protein design tasks, including providing control over designing of backbone structures (where the backbones are folded in a specified topology).

As described above, embodiments of the generative modeling techniques for arbitrary structure generation described herein include the use of diffusion models to generate structures. This includes using the models described herein for sequence design tasks, such as fixed backbone sequence design. As one example, suppose a structure to be re-engineered, such as to improve certain properties, such as increasing stability. The generative machine learning models described herein may be used to perform the entire sequence design task in a de novo fashion, "from scratch". Using the techniques described herein, AI (artificial intelligence) generated proteins can be created that can be validated in the laboratory context. For example, the models described herein may be used to, from a starting backbone with certain beta strands, design the amino acid sequence that will fold the protein into a certain structure.

Various design tasks are able to be accomplished primarily using embodiments of the generative model described herein. This is in contrast to existing generative techniques, which typically require additional steps such as guidance with an existing energy function, or substantial sampling to arrive at a single plausible solution.

As another example benefit of the techniques described herein, the generative model described herein is less limited in the types of structures that can be created. For example, existing techniques may be able to generate realistic samples, but only if limited to a particular shape or structure. For example, existing techniques involving models such as GANs (Generative Adversarial Networks) and VAEs (Variational Autoencoders) involve restricting to one particular topology class or domain, where the samples that are generated, though realistic, are self-similar to the restricted topology class. This is limiting (as it limits the variety of structures that can be generated), and is also associated with a number of failure modes, such as that the existing generative approaches are difficult to extend to larger and larger structures, as they are typically limited to a single domain. Comparison of Protein Diffusion Models and Image Diffusion Models Diffusion models for generating images (referred to herein as "image diffusion models"), such as Dall-E, have become increasingly popular. There are various differences between the protein diffusion models described herein for generating protein structures and diffusion models for generating images.

As one example, the training data is different. The training data for diffusion models for generating protein structures includes protein structure data.

As another example, the diffusion process is also different between image diffusion models and the protein diffusion models described herein. For example, in image diffusion models, the models diffuse toward a noise distribution, where the noise distribution is effectively Gaussian. As one example, an image is represented as a grid of pixel values, where, for example, each pixel value on the grid is a number scaled between −1 and 1. In image diffusion, the individual pixel values are noised toward a random value sampled from a Gaussian (e.g., 1D Gaussian). That is, there is a prior distribution, where if a sample is to be output from the generative model, a random Gaussian is sampled on a grid, where there is a random Gaussian for every pixel.

Such an approach as used in image diffusion models is not compatible with protein diffusion models, which are evaluating molecules in space, rather than evaluating pixels that have values between −1 and 1. Rather than diffusing a 2D image, a 3D structure is diffused. As described above, the protein diffusion model is evaluating coordinates that have different scaling. In addition, not only are coordinates represented, but also local 3D frames at each coordinate are represented. That is, local coordinate frames (rotational frames of reference) at each coordinate are used. Further embodiments and details of noising in the diffusion process are described above. Embodiments of protein diffusion processes described herein include diffusion processes for both 3D coordinates in 3D space, as well as processes for diffusing local coordinate frames.

Further, in the sampling process for image diffusion, the image is represented as a grid of a certain size. There is conditioning information, such as a text string. A random Gaussian is sampled at every element (e.g., a random 1D Gaussian at every pixel). A prediction is then made with the model, where diffusion is performed toward a prediction of the noise.

This is in contrast to diffusion for proteins (or components of proteins, such as structure, sequence, and/or rotamers), which are not grids of pixel values. To make the model invariant to rotation, random rotations are now sampled, which are, for example, uniform random from SU(2) or SO(3). This provides a way of interpolating between the predicted rotation frame at a given coordinate, and the current rotation frame. This is one example implementation of how diffusion may be performed for protein structures.

As another example difference, typically, the backbone of diffusion models for images has been U-Net convolutional network backbones, with a portion of the backbone having self-attention.

Such convolutional network backbones used in image diffusion models would not be applicable to the task of protein design, due to, for example, having to handle invariances (rotational and translational) and having to operate on protein objects. Further details regarding handling of rotational and translational invariance are described above.

As another example difference, the manner in which constraints are specified is tailored for protein design tasks. In some embodiments, techniques for designing proteins using diffusion models include techniques for encoding desired constraints. In image diffusion models, such as DALL-E, the constraints are embedded in a text string.

As described above, in embodiments of the protein diffusion model described herein, the constraints are specified based on representations of proteins with embeddable descriptive characteristics. As one example, proteins are represented as coarse blocks of structure, where allowed input constraints include definitions of adjacency (e.g., adjacency information between blocks), and where the protein modeling network is trained to evaluate such conditioning information and produce a protein structure. Further details and embodiments regarding encoding of constraints for a protein diffusion model are described above.

Additional Embodiments

Described herein are embodiments of a generative model of protein structures, sequences, and rotamers that can produce large protein structures that are both physically plausible and highly varied across all domain types (e.g., in the PDB). To this end, embodiments of a compact constraint specification are introduced which the model conditions on to produce highly-varied proteins. As shown in the examples above, the model's performance both qualitatively and quantitatively is demonstrated using biophysical metrics, as well is its potential for constructing variations on existing proteins, from re-sampling loops to varying the sizes of sub-structures. Also described above are details and embodiments regarding the model's ability to design sequences and pack rotamers, indicating its potential as a fully end-to-end tool for protein design.

The techniques described herein may also be used without constraints to perform unconditional generation of protein structure and sequence.

Figure 12:
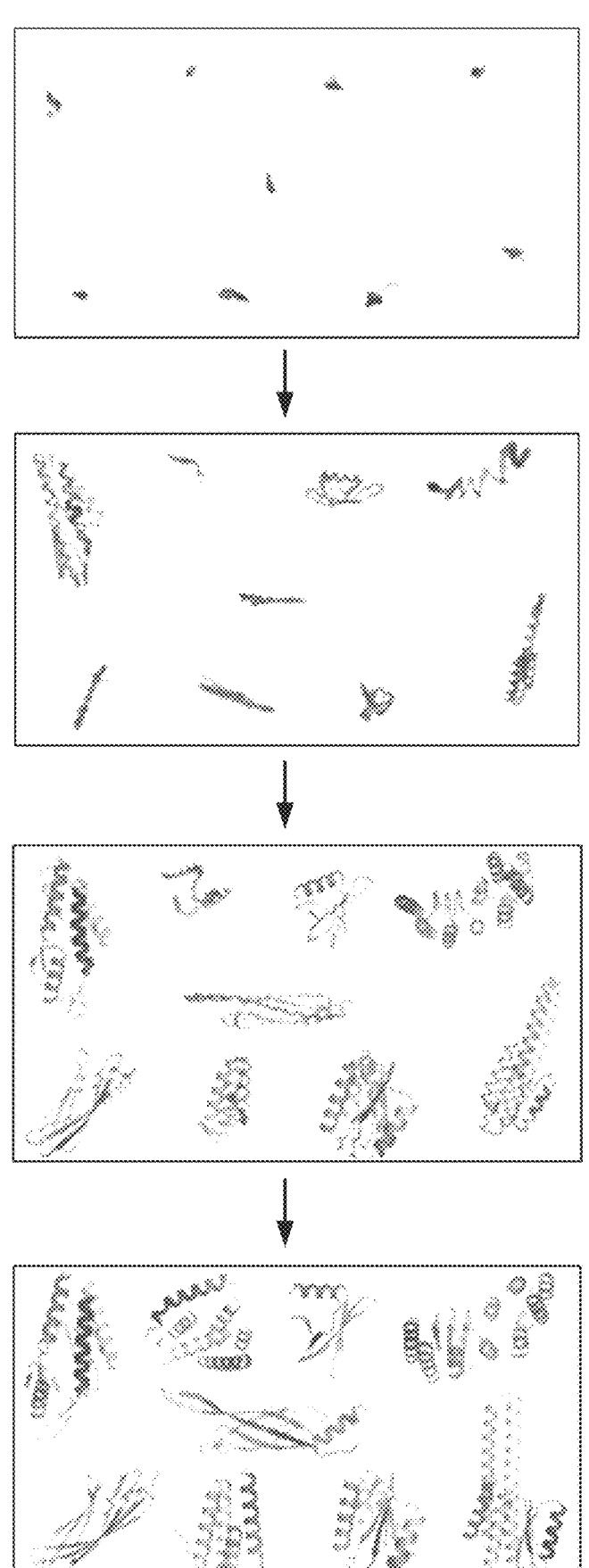
FIG. 12 illustrates an embodiment of a sampling process for unconditional protein structure generation.

FIG. 12 illustrates an embodiment of unconditional structure generation where no conditioning information is used, and random structures of various lengths, topologies, and characteristics are generated.

The techniques described herein can be used in a variety of ways. As a first example, it is straightforward to replace the "recycling" procedure for predictions in AlphaFold2 with the diffusion formulation described herein (or, replace the Constraints conditioning information with the output of, for example, Evoformer blocks). In predicting the structure of a protein there is often nontrivial aleatoric uncertainty, which arises from the fact that that there are often many conformations that the protein could adopt, of which only one is observed via crystallography. The model described herein introduces an elegant way of quantifying uncertainty, via, for example, measurement of the spread of samples, which may be of interest to practitioners as an additional signal beyond the per-residue uncertainty quantification made available by AlphaFold2.

Figure 13:
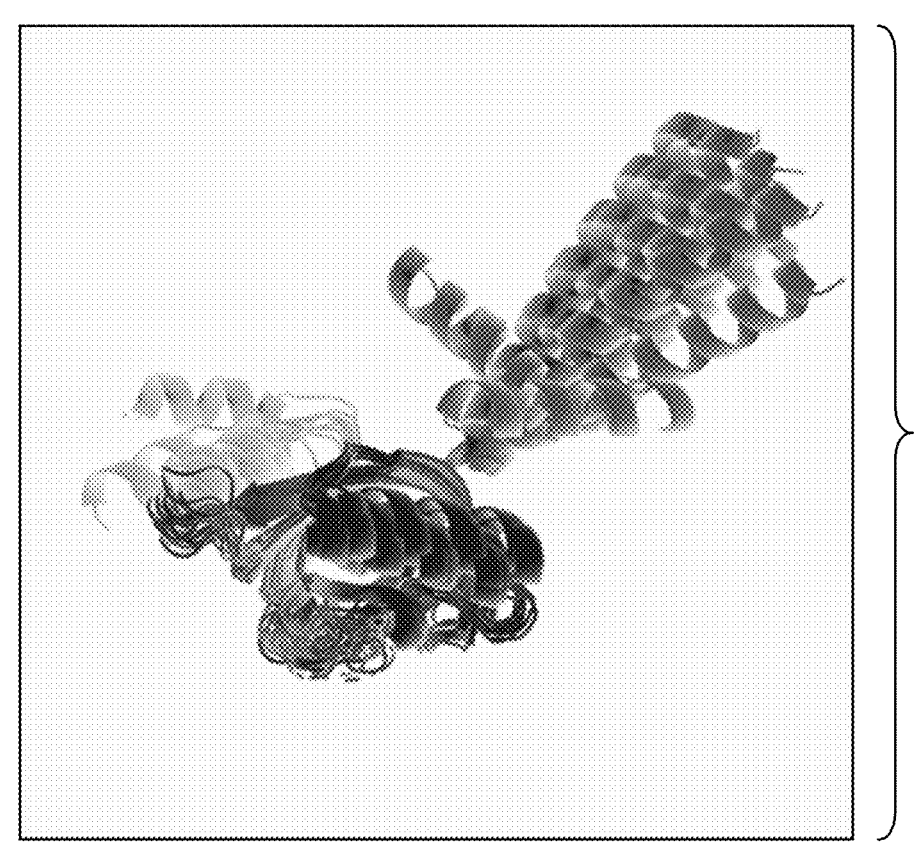
FIG. 13 illustrates an embodiment of multi-conformation structure prediction with diffusion models.
Figure 13:
Figure 13:
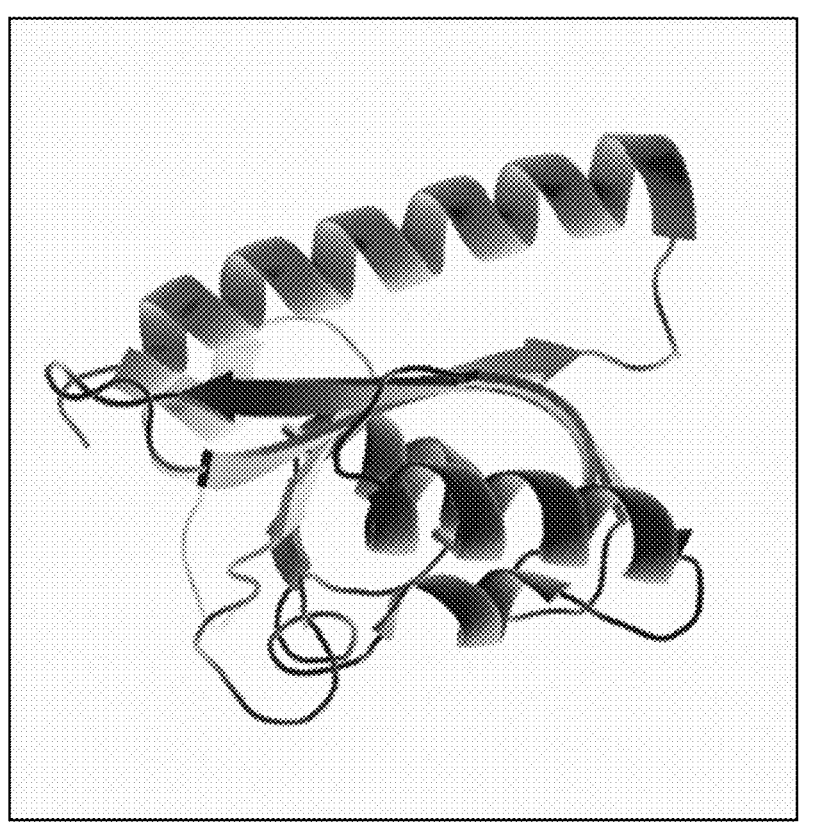

FIG. 13 illustrates an embodiment of a type of multi-conformation structure prediction, where for a given protein sequence, even if there is a single known crystal structure (1302) many possible structural modes are predicted (1304), illustrating where there is a higher degree of conformational flexibility in the molecule.

As a second example, classifier-free guidance can be used to interactively guide sampling for more fine-grained control over the sampling process. Embodiments of a compact constraint specification are described above to allow for easy specification as well as wide variance in the generated structures. However, given a generated structure, classifier-free guidance can be used to leverage auxiliary energy functions, e.g., gradients of distance constraints on atoms, to make precise modifications while ensuring global consistency with the rest of the structure.

As a third example, embodiments of models described herein can be used in applications such as fitting proteins to X-ray crystallography electron densities or Cryo-EM volumes. Existing approaches typically use auto-regressive methods to iteratively fit structures, which face limitations when the volumes are ambiguous and backtracking becomes necessary to correct for mistakes earlier in the autoregressive process. The protein diffusion model described herein, which forms the structure globally during sampling, can help mitigate these failure modes.

Figure 14:
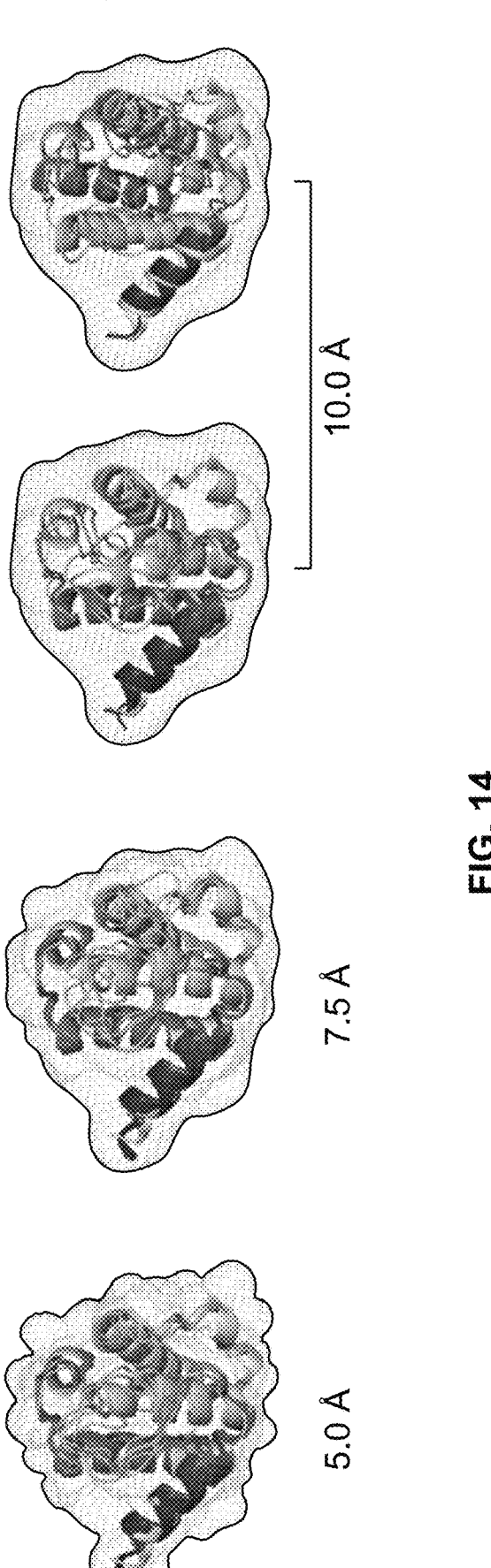
FIG. 14 illustrates an embodiment of fitting atomic models to electron densities with diffusion models.

FIG. 14 illustrates an embodiment of fitting proteins to electron densities with diffusion models that simultaneously predict the structure of the protein from sequence and find a global orientation of the molecule that fits the volume.

As a fourth example, the diffusion techniques and approaches described herein may be variously adapted to facilitate RNA (ribonucleic acid) structure prediction and design.

As a fifth example, embodiments of the approach described herein may be variously adapted for designing proteins that can bind to other proteins based on the 3D structure and chemical composition of the target protein.

Figure 15:
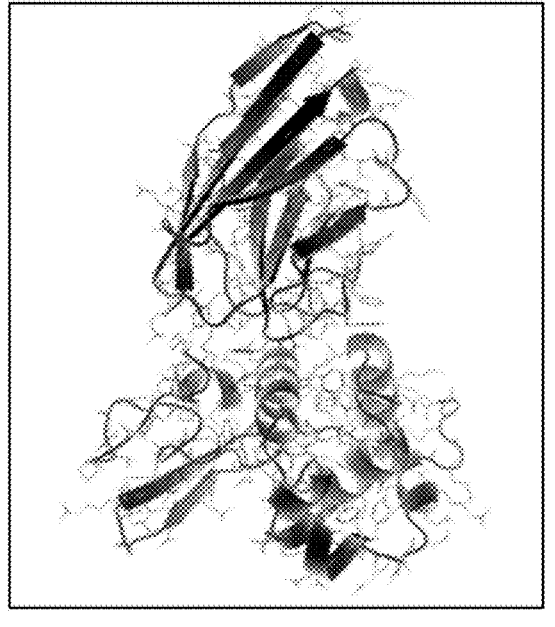
FIG. 15 illustrates an embodiment of designing binders to a target protein.
Figure 15:
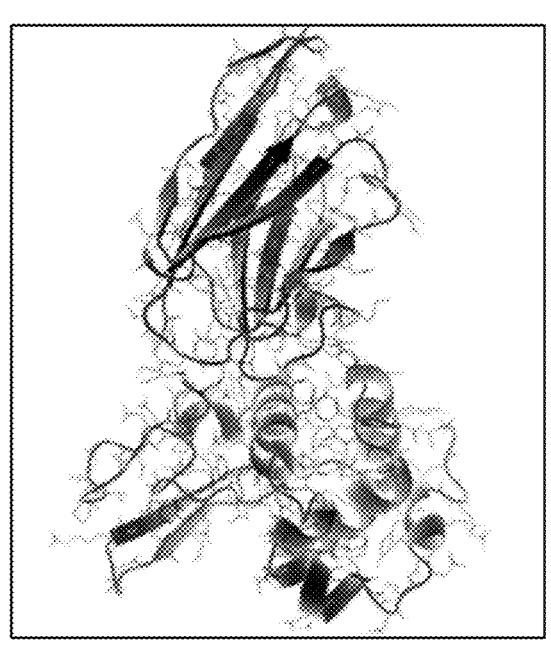
Figure 15:
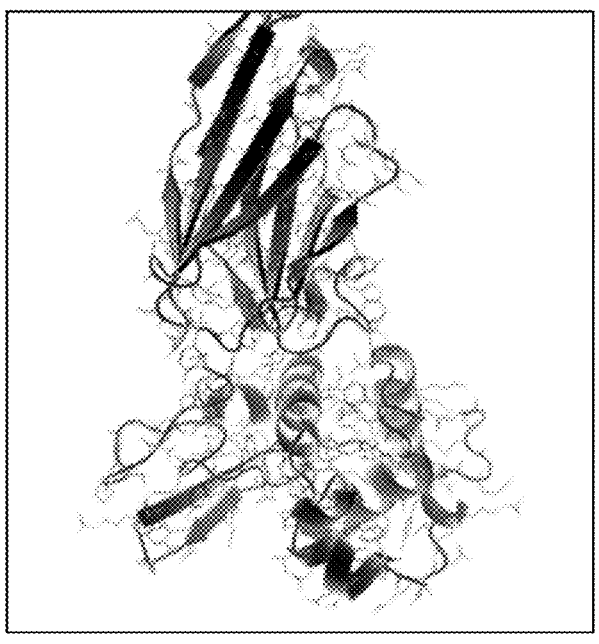
Figure 15:
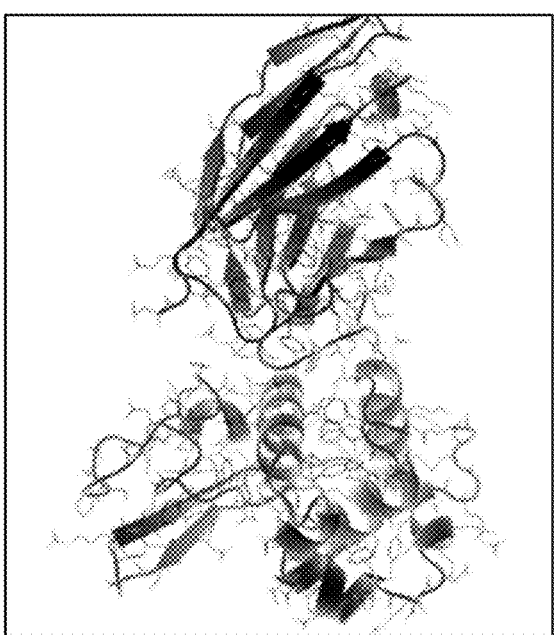

FIG. 15 illustrates an embodiment of designing protein binders to a target protein, where the target protein's structure is predicted while simultaneously the structure and sequence of a target protein are generated with a diffusion model. Multiple, highly varying designs can be made against the same epitope (position on the target protein).

As a sixth example, embodiments of the approach described herein may be variously adapted to facilitate designing small molecules to bind to proteins.

The generative techniques for engineering proteins may be variously adapted to accommodate engineering of other types of compounds.

As one example, the techniques described herein may be used to facilitate drug development, such as identifying a protein that can bind with a target protein.

As another example, the generative techniques described here may be adapted to facilitate enzyme engineering. Enzymes are examples of proteins that can catalyze chemical reactions. By controllably creating enzymes, new types of reactions may be catalyzed, allowing chemistry to be performed in a more efficient, and less resource intensive, manner. As another example of enzyme engineering, the generative techniques described herein may be used to generate new biofuels or ways to break down plastics or other materials.

Figure 16:
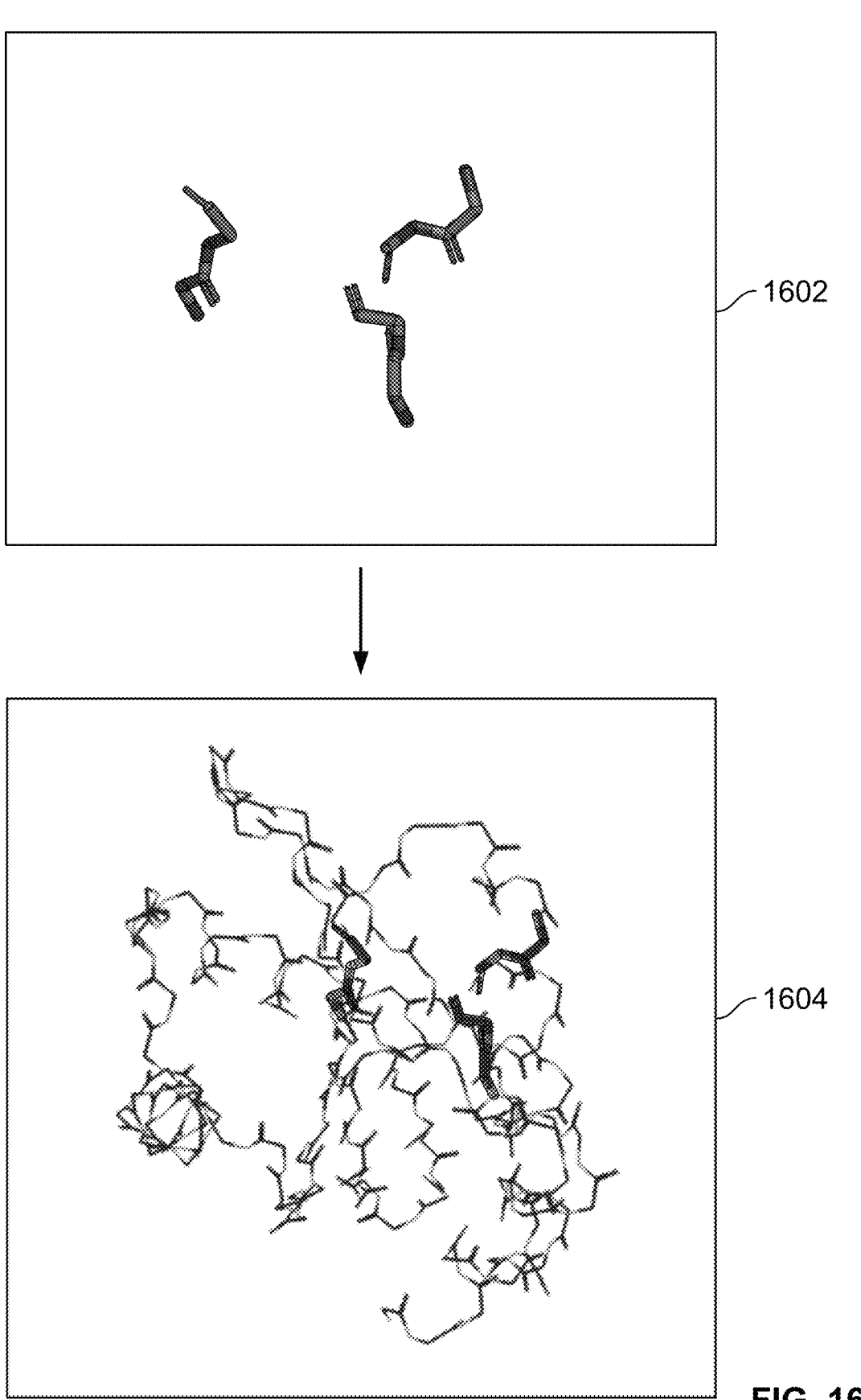
FIG. 16 illustrates an embodiment of generating enzyme scaffolds with diffusion models.

FIG. 16 is a diagram illustrating an embodiment of starting with fixed constraints (1602) and then using the diffusion model to generate an enzyme scaffold (1604), simulating how to design an enzyme given functional or positional constraints of the enzyme substrate and active site residues.

The generative techniques described herein may also be used to facilitate creation of therapeutics. Much of therapeutics involves creating compounds that are able to bind to a target in a person's body, such in cells or on the outside of a cell. Using the generative techniques described herein, various candidate designs may be modeled, such as proteins or small molecules interacting with a protein target.

Further, toxicity may be modeled, such as whether a person's immune system will have a reaction, or immunogenicity, to a protein or molecule. Pharmacokinetics of how a molecule interacts with a body may also be modeled.

The generative techniques described herein may also be used to facilitate diagnostics. For example, proteins may be engineered or designed to bind to certain proteins to develop tests for detecting certain illnesses. As one example, proteins may be generated to bind to the COVID spike protein, allowing for a faster detection mechanism. Proteins for detecting other types of molecules, such as opioids, may also be modeled and engineered using the techniques described herein.

In various embodiments, the generative techniques described herein are used to design antigens in order to develop therapeutic molecules. Antigens (proteins that trigger an immune response) can be used to immunize animals, leading to, for example, generation of antibodies, nanobodies, or other immune system proteins that bind to the antigen of interest. Certain antigens do not lead to generation of these immune system molecules against the desired epitopes (or regions on the antigen). Using generative design to remodel the antigen may improve production of immune system molecules against desired epitopes.

As described above, using embodiments of the generative techniques described herein, molecules or compounds of various configurations with various functions can be efficiently engineered and controlled.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method, comprising:
   expressing, in a laboratory setting, an amino acid sequence, wherein the amino acid sequence was generated as output of a protein diffusion model, wherein the amino acid sequence is predicted by the protein diffusion model to fold to a desired backbone structure, and wherein generating the amino acid sequence using the protein diffusion model comprises:
   receiving a representation of a protein as training data, the representation comprising at least three dimensions, and wherein the representation of the protein comprises, for an atom of a backbone structure of the protein, a corresponding coordinate and a corresponding coordinate frame;
   training the protein diffusion model on at least one graphics processing unit (GPU) at least in part by performing rotational diffusion based at least in part on the representation of the protein; and
   using the protein diffusion model to generate a binder to a target protein included in protein conditioning information that is received as input, wherein an evaluation of the binder generated for the target protein included in the protein conditioning information is performed, including evaluating a delta energy corresponding to interacting of the binder generated using the protein diffusion model and the target protein included in the protein conditioning information received as input, and wherein generating the binder comprises generating the amino acid sequence.

2. The method of claim 1, wherein performing the rotational diffusion comprises performing interpolation between rotations.

3. The method of claim 2, wherein performing the interpolation comprises interpolating between rotational frames of reference.

4. The method of claim 1, wherein training the protein diffusion model comprises determining one or more parameters of the protein diffusion model based at least in part on the rotational diffusion and computing of a loss.

5. The method of claim 4, wherein computing the loss comprises aligning coordinate frames.

6. The method of claim 1, wherein the representation of the protein comprises angles associated with rotamers.

7. A method, comprising:
   expressing, in a laboratory setting, an amino acid sequence, wherein the amino acid sequence was generated as output of a protein diffusion model, wherein the amino acid sequence is predicted by the protein diffusion model to fold to a desired backbone structure, and wherein generating the amino acid sequence using the protein diffusion model comprises:

receiving, as input, protein conditioning information including a target protein;

based at least in part on the protein conditioning information, performing conditional sampling of the protein diffusion model, wherein the protein diffusion model is trained on at least one graphics processing unit (GPU) at least in part by performing rotational diffusion based at least in part on a representation of a protein comprising, for an atom of a backbone structure of the protein, a corresponding coordinate and a corresponding coordinate frame;

wherein based at least in part on the conditional sampling of the protein diffusion model, the protein diffusion model generates a binder to the target protein included in the protein conditioning information that is received as input, and wherein generating the binder using the protein diffusion model comprises generating the amino acid sequence; and performing an evaluation of the binder generated for the target protein included in the protein conditioning information, including evaluating a delta energy corresponding to interacting of the binder generated using the protein diffusion model and the target protein included in the protein conditioning information received as input.

8. The method of claim 7, wherein the protein conditioning information comprises an indication of protein residues.

9. The method of claim 8, wherein the protein conditioning information comprises an indication of blocks into which the protein residues are divided.

10. The method of claim 9, wherein the protein conditioning information comprises a block secondary structure assignment.

11. The method of claim 9, wherein the protein conditioning information comprises block adjacency information.

12. The method of claim 11, wherein the block adjacency information comprises an indication of adjacency or non-adjacency between two blocks.

13. The method of claim 10 wherein the protein conditioning information comprises an indication of whether a beta sheet pairing is parallel or anti-parallel.

14. The method of claim 7, further comprising:

performing the conditional sampling of the protein diffusion model at least in part by:

determining a plurality of noise samples; and for each noise sample in the plurality of noise samples, conditionally sampling the protein diffusion model using the noise sample and the protein conditioning information; and wherein a plurality of binders are generated by the protein diffusion model.

* * * * *